US012811009B2

(12) United States Patent
Anand et al.

(10) Patent No.: US 12,811,009 B2
(45) Date of Patent: Nov. 24, 2026

(54) LEARNABLE VISUAL PROMPT ENGINEERING

(71) Applicant: GE Precision Healthcare LLC, Waukesha, WI (US)

(72) Inventors: Deepa Anand, Bangalore (IN); Dattesh Shanbhag, Bengaluru (IN); Hariharan Ravishankar, Bengaluru (IN); Suresh Emmanuel Devadoss Joel, Bangalore (IN); Rakesh Mullick, Bangalore (IN); Rachana Sathish, Bengaluru (IN); Rahul Venkataramani, Bengaluru (IN); Krishna Seetharam Shriram, Bengaluru (IN); Prasad Sudhakara Murthy, Bengaluru (IN)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 371 days.

(21) Appl. No.: 18/504,649

(22) Filed: Nov. 8, 2023

(65) Prior Publication Data

US 2025/0149169 A1 May 8, 2025

(51) Int. Cl.

*G16H 50/20* (2018.01)
*G06T 7/00* (2017.01)
*G16H 30/40* (2018.01)

(52) U.S. Cl.

CPC ........... *G16H 50/20* (2018.01); *G06T 7/0012* (2013.01); *G16H 30/40* (2018.01);
(Continued)

(58) Field of Classification Search

CPC ...... G16H 30/40; G16H 50/20; G06T 7/0012; G06T 2207/20081; G06T 2207/20084; G06T 2207/30004
See application file for complete search history.

(56) References Cited

U.S. PATENT DOCUMENTS 11,151,719 B2 10/2021 Karki et al.
12,444,172 B2 * 10/2025 Venkataramani .... G06V 10/774
(Continued)

OTHER PUBLICATIONS

Lee, H. et al. | "Practical window setting optimization for medical image deep learning." Machine Learning for Health (ML4H) Workshop, NeurIPS, 2018, arXiv reprint: arXiv:1812.00572v1 [cs.CV] Dec. 3, 2018, 8 pages.
(Continued)

*Primary Examiner* — Ping Y Hsieh
*Assistant Examiner* — Jose M Torres
(74) *Attorney, Agent, or Firm* — Amin, Turocy & Watson, LLP

(57) ABSTRACT

Systems or techniques for facilitating learnable visual prompt engineering are provided. In various embodiments, a system can access a medical image and a pre-trained machine learning model that is configured to perform a diagnostic or prognostic inferencing task. In various aspects, the system can apply a pre-processing transformation to one or more pixels or voxels of the medical image, thereby yielding a transformed version of the medical image, wherein the pre-processing transformation can convert an input pixel or voxel intensity value to an output pixel or voxel intensity value via one or more parameters that are iteratively learned. In various instances, the system can perform the diagnostic or prognostic inferencing task, by executing the pre-trained machine learning model on the transformed version of the medical image.

20 Claims, 23 Drawing Sheets

(52) U.S. Cl.
CPC ............... *G06T 2207/20081* (2013.01); *G06T 2207/20084* (2013.01); *G06T 2207/30004* (2013.01)

(56) References Cited

U.S. PATENT DOCUMENTS

| | | | | |
|---|---|---|---|---|
| 12,597,238 | B2 * | 4/2026 | Dong | G06V 10/774 |
| 2009/0010521 | A1 * | 1/2009 | Ramsay | G06V 10/255<br>382/141 |
| 2018/0241929 | A1 * | 8/2018 | Bouzaraa | H04N 23/741 |
| 2019/0095810 | A1 * | 3/2019 | Chakraborty | G06N 7/01 |
| 2020/0160974 | A1 * | 5/2020 | Yao | G06F 18/41 |
| 2023/0071535 | A1 * | 3/2023 | Abrol | G06V 10/25 |
| 2025/0086941 | A1 * | 3/2025 | Amthor | G06V 10/82 |

OTHER PUBLICATIONS

Karki, M. et al. | "CT window trainable neural network for improving intracranial hemorrhage detection by combining multiple settings." Artificial Intelligence in Medicine, 106 (2020) 101850, https://doi.org/10.1016/j.artmed.2020.101850, 8 pages.
Huo, Y. et al. | "Stochastic tissue window normalization of deep learning on computed tomography." J. Med. Imag. 6 (4), 044005 (2019), doi: 10.1117/1.JMI.6.4.044005, 13 pages.
Bommasani, R. et al. | "On the opportunities and risks of foundation models." arXiv:2108.07258v3 [cs.LG] Jul. 12, 2022, 214 pages.
Padhani, A.R. et al. | "METastasis reporting and data system for prostate cancer: practical guidelines for acquisition, interpretation, and reporting of whole-body magnetic resonance imaging-based evaluations of multiorgan involvement in advanced prostate cancer." European urology, Jan. 2017, 71(1), pp. 81-92, 23 pages.

* cited by examiner

700

1100

1200

1300

1500

1500

1700

1800

1900

2000

LEARNABLE VISUAL PROMPT ENGINEERING

TECHNICAL FIELD

The subject disclosure relates generally to machine learning, and more specifically to learnable visual prompt engineering.

BACKGROUND

A machine learning model can be trained in supervised fashion to perform a visual inferencing task on inputted medical images. After being trained, the machine learning model can be deployed in the field, so as to perform the visual inferencing task on inputted medical images that lack ground-truth annotations. During deployment, it can be desired to implement the machine learning model on medical images that belong to a new domain that is different from that on which the machine learning model was trained. Existing techniques facilitate such implementation by retraining or fine-tuning the machine learning model on annotated medical images from the new domain. Unfortunately, such retraining or fine-tuning can be excessively time-consuming and computationally expensive.

SUMMARY

The following presents a summary to provide a basic understanding of one or more embodiments. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus or computer program products that facilitate learnable visual prompt engineering are described.

According to one or more embodiments, a system is provided. The system can comprise a non-transitory computer-readable memory that can store computer-executable components. The system can further comprise a processor that can be operably coupled to the non-transitory computer-readable memory and that can execute the computer-executable components stored in the non-transitory computer-readable memory. In various embodiments, the computer-executable components can comprise an access component that can access a medical image and a pre-trained machine learning model that is configured to perform a diagnostic or prognostic inferencing task. In various aspects, the computer-executable components can comprise a visual prompt engineering component that can apply a pre-processing transformation to one or more pixels or voxels of the medical image, thereby yielding a transformed version of the medical image, wherein the pre-processing transformation can convert an input pixel or voxel intensity value to an output pixel or voxel intensity value via one or more parameters that are iteratively learned. In various instances, the computer-executable components can comprise an execution component that can perform the diagnostic or prognostic inferencing task, by executing the pre-trained machine learning model on the transformed version of the medical image.

According to one or more embodiments, a computer-implemented method is provided. In various embodiments, the computer-implemented method can comprise accessing, by a device operatively coupled to a processor, a medical image and a pre-trained machine learning model that is configured to perform a diagnostic or prognostic inferencing task. In various aspects, the computer-implemented method can comprise applying, by the device, a pre-processing transformation to one or more pixels or voxels of the medical image, thereby yielding a transformed version of the medical image, wherein the pre-processing transformation can convert an input pixel or voxel intensity value to an output pixel or voxel intensity value via one or more parameters that are iteratively learned. In various instances, the computer-implemented method can comprise performing, by the device, the diagnostic or prognostic inferencing task, by executing the pre-trained machine learning model on the transformed version of the medical image.

According to one or more embodiments, a computer program product for facilitating learnable visual prompt engineering is provided. In various embodiments, the computer program product can comprise a non-transitory computer-readable memory having program instructions embodied therewith. In various aspects, the program instructions can be executable by a processor to cause the processor to access an image. In various instances, the program instructions can be further executable to cause the processor to generate an adapted version of the image via a pixel-to-pixel or voxel-to-voxel pre-processing transformation comprising one or more parameters that are iteratively learned. In various cases, the program instructions can be further executable to cause the processor to perform a visual inferencing task, by executing a pre-trained machine learning model on the adapted version of the image.

DETAILED DESCRIPTION

Figure 1:
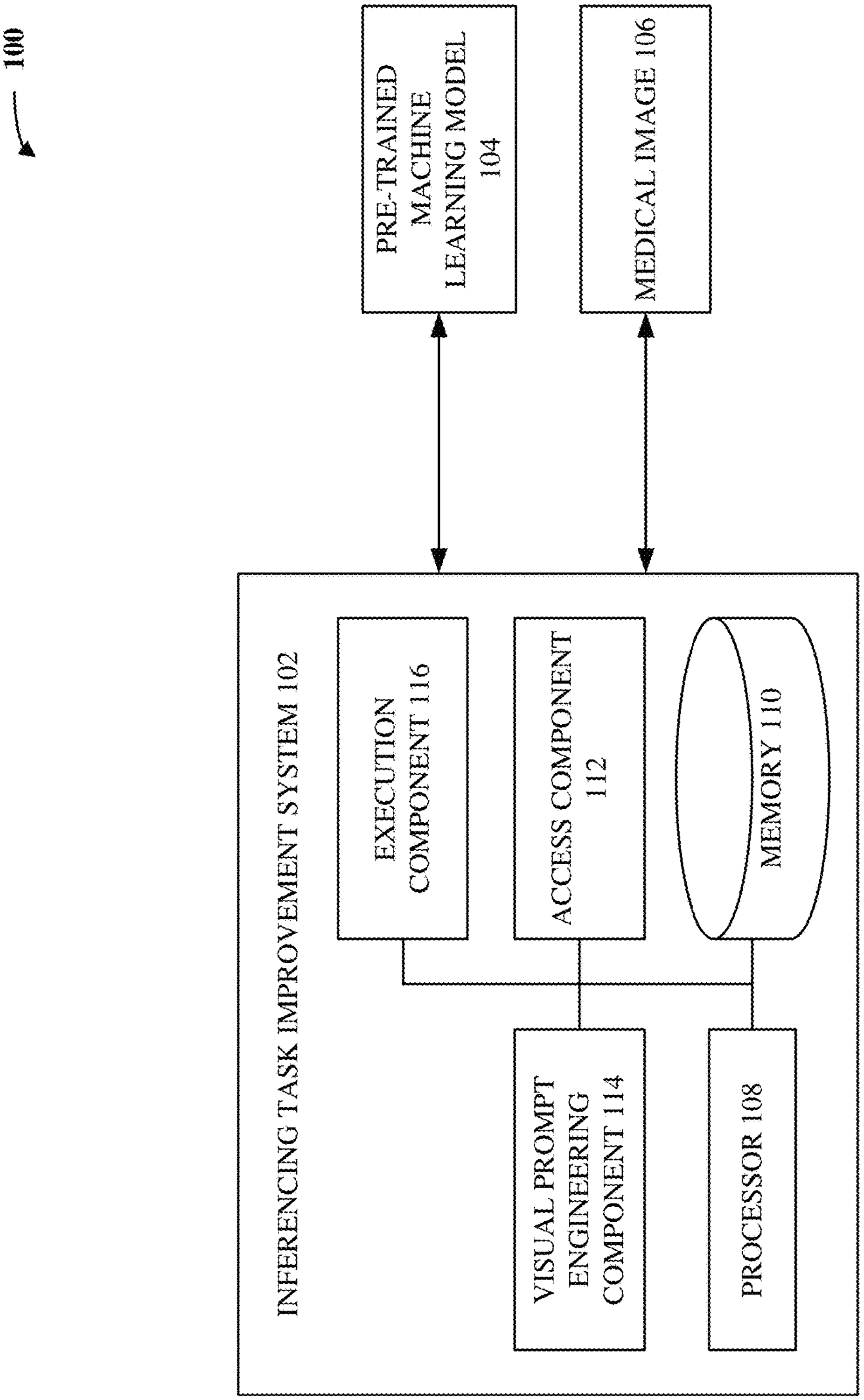
FIG. 1 illustrates a block diagram of an example, non-limiting system that facilitates learnable visual prompt engineering in accordance with one or more embodiments described herein.

The following detailed description is merely illustrative and is not intended to limit embodiments or application/uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

A machine learning model (e.g., a deep learning neural network) can be trained in supervised fashion to perform a visual inferencing task (e.g., image classification, image segmentation, image regression) on inputted medical images, where a medical image can be an image that depicts any suitable anatomical structure of a medical patient and that was captured or generated by any suitable medical imaging scanner (e.g., by a computed tomography (CT) scanner, by a magnetic resonance imaging (MRI) scanner, by an X-ray scanner, by an ultrasound scanner, by a positron emission tomography (PET) scanner). After being trained, the machine learning model can be deployed in the field, so as to perform the visual inferencing task on inputted medical images that lack ground-truth annotations.

During deployment, it can be desired to implement the machine learning model on medical images that belong to a new domain that is different from an original domain on which the machine learning model was trained. In particular, the medical images on which the machine learning model was trained can exhibit various visually stylistic characteristics (e.g., various brightness levels, various contrast levels, various blurring levels, various types of visual textures), and such visually stylistic characteristics can be considered as collectively forming or defining the original domain that the machine learning model was trained to handle (e.g., as trained to accurately or reliably analyze). Medical images whose visually stylistic characteristics are sufficiently different or dissimilar from those of the original domain can be considered as belonging to a new domain which the machine learning model was not trained to handle. Because the machine learning model was not trained on the visually stylistic characteristics of the new domain, the machine learning model can be unable to accurately or reliably perform the visual inferencing task on medical images belonging to the new domain.

Existing techniques attempt to address this issue by retraining or fine-tuning the machine learning model on annotated medical images that belong to the new domain. Unfortunately, however, such retraining or fine-tuning can be excessively time-consuming and computationally expensive. Indeed, the machine learning model can have hundreds of thousands, millions, or even billions of trainable internal parameters (e.g., weight matrices, bias values, convolutional kernels). Retraining or fine-tuning such voluminous trainable internal parameters can consume a significant amount of computing time (e.g., hours, days, weeks) and processing capacity (e.g., tens or hundreds of gigabytes, or even terabytes). Moreover, retraining or fine-tuning such voluminous trainable internal parameters can require a commensurately voluminous amount of annotated medical images from the new domain (e.g., on the order of thousands or millions of annotated medical images), and curation or acquisition of such voluminous amount of annotated medical images can be extremely tedious and time-consuming for operators or technicians overseeing the machine learning model.

Accordingly, systems or techniques that can enable the machine learning model to handle medical images belonging to the new domain without excessive computational cost can be desirable.

Various embodiments described herein can address one or more of these technical problems. One or more embodiments described herein can include systems, computer-implemented methods, apparatus, or computer program products that can facilitate learnable visual prompt engineering. In particular, the inventors of various embodiments described herein devised various techniques that can enable a machine learning model to perform a visual inferencing task on out-of-domain medical images, without incurring the excessive computational costs associated with retraining or fine-tuning the machine learning model.

More specifically, various embodiments described herein can include implementing a pre-processing image transformation in conjunction with the machine learning model. The pre-processing image transformation can be any suitable linear, non-linear, or other function or operation that can convert an inputted pixel (or voxel) intensity value to an outputted pixel (or voxel) intensity value by leveraging one or more learnable parameters (e.g., one or more learnable scalar coefficients that can be additively or multiplicatively applied to a pixel (or voxel) intensity value). Note that, in various aspects, the pre-processing image transformation can comprise, in total, many orders of magnitude fewer learnable parameters than the machine learning model (e.g., the machine learning model can have millions of parameters, whereas the pre-processing image transformation can have two parameters, three parameters, or an otherwise small handful of parameters). As described herein, the learnable parameters of the pre-processing image transformation can be iteratively trained in supervised fashion or on-the-fly, so as to boost performance of the machine learning model. In other words, when executed post-training on all of the pixels (or voxels) of any given medical image, the pre-processing image transformation can be considered as causing that given medical image to exhibit the visually stylistic characteristics of the original domain on which the machine learning model was trained, thereby enabling the machine learning model to accurately or reliably perform the visual inferencing task on that given medical image. In still other words, the pre-processing image transformation can be considered as being trained to adapt or otherwise engineer (hence the term "visual prompt engineering") the given medical image so that it can be more easily handled or analyzed by the machine learning model. In any case, note that the parameters of the machine learning model can be frozen or otherwise unaltered during such training. Moreover, note that, because the pre-processing image transformation can comprise many orders of magnitude fewer parameters than the machine learning model, training of the pre-processing image transformation as described herein can consume many orders of magnitude less time, and can require many orders of magnitude less training data or fewer training iterations, than retraining or fine-tuning of the machine learning model itself. In this way, various embodiments described herein can enable the machine learning model to accurately or reliably perform the visual inferencing task on medical images that it otherwise would not be able to handle, without incurring the excessive computational costs associated with retraining or fine-tuning of the machine learning model.

Various embodiments described herein can be considered as a computerized tool (e.g., any suitable combination of computer-executable hardware or computer-executable software) that can facilitate learnable visual prompt engineering. In various aspects, such computerized tool can comprise an access component, a visual prompt engineering component, or an execution component.

In various embodiments, there can be a particular medical image. In various aspects, the particular medical image can exhibit any suitable format, size, or dimensionality (e.g., the particular medical image can be a two-dimensional pixel array, or the particular medical image can be a three-dimensional voxel array). In various instances, the particular medical image can visually depict any suitable anatomical structure (e.g., tissue, organ, body part, or portion thereof) of any suitable medical patient. In various cases, the particular medical image can be generated or captured by any suitable medical imaging modality or equipment (e.g., generated or captured by a CT scanner, by an MRI scanner, by an X-ray scanner, by an ultrasound scanner, or by a PET scanner).

In various embodiments, there can be a foundational model. In various aspects, the foundational model can exhibit any suitable machine learning architecture, such as a deep learning internal architecture. For example, the foundational model can include any suitable numbers of any suitable types of layers (e.g., input layer, one or more hidden layers, output layer, any of which can be convolutional layers, dense layers, non-linearity layers, pooling layers, batch normalization layers, or padding layers). As another example, the foundational model can include any suitable numbers of neurons in various layers (e.g., different layers can have the same or different numbers of neurons as each other). As yet another example, the foundational model can include any suitable activation functions (e.g., softmax, sigmoid, hyperbolic tangent, rectified linear unit) in various neurons (e.g., different neurons can have the same or different activation functions as each other). As still another example, the foundational model can include any suitable interneuron connections or interlayer connections (e.g., forward connections, skip connections, recurrent connections).

Regardless of its internal architecture, the foundational model can be configured to perform a visual inferencing task on inputted medical images. In various aspects, the visual inferencing task can be any suitable computational, predictive task that can be performed on or with respect to medical images. As some non-limiting examples, the visual inferencing task can be image classification (e.g., classifying or diagnosing pathologies depicted in medical images), image segmentation (e.g., localizing boundaries of anatomical structures or surgical implants depicted in medical images), or image regression (e.g., denoising or enhancing resolutions of medical images, so as to aid diagnosis).

In various embodiments, the foundational model can be trained in supervised fashion to perform the visual inferencing task. In various aspects, such supervised training can be based on a dataset comprising medical images each having the same format, size, or dimensionality as the particular medical image and each corresponding to a respective ground-truth annotation. In various aspects, a ground-truth annotation can be any suitable electronic data that indicates a correct or accurate visual inferencing task result that is known or deemed to correspond to a respective medical image in the dataset. Accordingly, the format, size, or dimensionality of a ground-truth annotation can depend upon the visual inferencing task that the foundational model is configured to perform (e.g., if the visual inferencing task is image classification, then each ground-truth annotation can be a correct or accurate classification label corresponding to a respective medical image in the dataset; if the visual inferencing task is image segmentation, then each ground-truth annotation can be a correct or accurate segmentation mask corresponding to a respective medical image in the dataset; if the visual inferencing task is image regression, then each ground-truth annotation can be a correct or accurate regression result corresponding to a respective medical image in the dataset).

In various aspects, the particular medical image can be considered as being out-of-domain with respect to the dataset on which the foundational model was trained. That is, the particular medical image can exhibit various visually stylistic characteristics (e.g., brightness, contrast, blurriness, texture, or other underlying optical patterns), and such visually stylistic characteristics can be unlike those exhibited by the dataset on which the foundational model was trained. Accordingly, the foundational model can be unable to accurately or reliably perform the visual inferencing task on the particular medical image.

Despite the particular medical image being out-of-domain, it can nevertheless be desired to accurately or reliably perform the visual inferencing task on or otherwise with respect to the particular medical image, without retraining or fine-tuning the foundational model. The computerized tool described herein can facilitate such performance.

In various embodiments, the access component of the computerized tool can electronically receive or otherwise electronically access the foundational model or the particular medical image. In some aspects, the access component can electronically retrieve the foundational model or the particular medical image from any suitable centralized or decentralized data structures (e.g., graph data structures, relational data structures, hybrid data structures), whether remote from or local to the access component. In any case, the access component can electronically obtain or access the foundational model or the particular medical image, such that other components of the computerized tool can electronically interact with (e.g., read, write, edit, copy, manipulate) the foundational model or with the particular medical image.

In various embodiments, the visual prompt engineering component of the computerized tool can electronically generate an adjusted version of the particular medical image on which the foundational model can more accurately or reliably perform the visual inferencing task.

More specifically, the visual prompt engineering component can electronically store, maintain, control, or otherwise access a pre-processing transformation. In various aspects, the pre-processing transformation can be any suitable pixel-to-pixel (or voxel-to-voxel) function that can receive as an argument an inputted pixel (or voxel) intensity value and that can convert that inputted pixel (or voxel) intensity value into an outputted pixel (or voxel) intensity value. In various instances, the pre-processing transformation can facilitate such conversion via one or more trainable parameters that can be iteratively learned. In various cases, such trainable parameters can be scalar coefficients that can be added to, be subtracted from, be multiplied by, serve as divisors for, serve as dividends for, serve as exponents for, serve as roots for, or be otherwise mathematically applied to the inputted pixel (or voxel) intensity value, so as to numerically compute the outputted pixel (or voxel) intensity value. In various aspects, the pre-processing transformation can have a computational footprint that is many orders of magnitude smaller (e.g., thousands of times smaller or millions of times smaller) than that of the foundational model. Indeed, as a non-limiting example, the pre-processing transformation can operate on individual pixels (or voxels) one at a time and can have five or fewer trainable parameters in total. Contrast this with the foundational model, which can instead operate on entire medical images (e.g., large arrays of pixels or voxels) and can have thousands, millions, or even billions of trainable parameters.

In any case, the one or more trainable parameters of the pre-processing transformation can have values or magnitudes that are iteratively learned, so as to preserve visual content of medical images while simultaneously altering visually stylistic characteristics of medical images to boost or otherwise improve the inferencing performance of the foundational model. As described later herein, such iterative learning can be conducted in supervised fashion based on annotated medical images having similar visually stylistic characteristics as the particular medical image, or such iterative learning can instead be conducted on-the-fly (e.g., at inferencing time, without annotated images) based on an auxiliary confidence predictor that can generate confidence scores for visual inferencing task results produced by the foundational model.

In various instances, after the one or more trainable parameters of the pre-processing transformation are iteratively learned, the visual prompt engineering component can apply the pre-processing transformation to each pixel (or voxel) of the particular medical image, and such application can be considered as yielding an adjusted or transformed version of the particular medical image. More specifically, for any given pixel (or voxel) of the particular medical image, the visual prompt engineering component can apply the pre-processing transformation to the intensity value (e.g., Hounsfield unit value) of that given pixel (or voxel), and such application can compute or calculate a new or resultant intensity value for that given pixel (or voxel). Application of the pre-processing transformation to each pixel (or voxel) of the particular medical image can yield a plurality of new or resultant intensity values (e.g., one distinct new or resultant intensity value per pixel or per voxel). In various cases, such plurality of new or resultant intensity values can collectively be considered as forming the adapted or transformed version of the particular medical image. In other words, such plurality of new or resultant intensity values can be considered as collectively forming another image, where such another image can have the same format, size, or dimensionality as the particular medical image, where such another image can depict the same visual content (e.g., the same anatomical structure of the same medical patient) as the particular medical image, but where such another image can exhibit different visually stylistic characteristics (e.g., contrast, brightness, texture) than the particular medical image.

In various embodiments, the execution component of the computerized tool can electronically execute the foundational model on the adapted or transformed version of the particular medical image, rather than on the particular medical image itself. Such execution can yield a visual inferencing task result. More specifically, the execution component can feed the adapted or transformed version of the particular medical image to an input layer of the foundational model, the adapted or transformed version of the particular medical image can complete a forward pass through one or more hidden layers of the foundational model, and an output layer of the foundational model can compute the visual inferencing task result based on activations provided by the one or more hidden layers. Note that the visual inferencing task result can be any suitable electronic data whose format, size, or dimensionality can depend upon the visual inferencing task that the foundational model is configured to perform (e.g., the visual inferencing task result can be a predicted or inferred classification label, a predicted or inferred segmentation mask, or a predicted or inferred regression output that the foundational model has generated for the adapted or transformed version of the particular medical image).

Due to the pre-processing transformation, it can be the case that an accuracy level, precision level, or reliability level of the visual inferencing task result is higher than what would be achieved if the foundational model were instead executed directly on the particular medical image. As mentioned above, the particular medical image can be out-of-domain with respect to the data on which the foundational model was trained, meaning that the foundational model would not generate an accurate, precise, or reliable visual inferencing task result if it were executed directly on the particular medical image. However, as also mentioned above, the pre-processing transformation can, as described herein, be trained so as to alter or engineer visually stylistic characteristics of the particular medical image, where such altered or engineered visually stylistic characteristics boost performance of the foundational model. In other words, the pre-processing transformation can cause the adapted or transformed version of the particular medical image to illustrate the same visual content (e.g., same anatomical structures) as the particular medical image but to simultaneously exhibit visually stylistic characteristics (e.g., brightness, contrast, texture) that are altered to be more amenable to analysis by the foundational model. Thus, although the particular medical image cannot be accurately, precisely, or reliably analyzed by the foundational model, the adapted or transformed version of the particular medical image can be accurately, precisely, or reliably analyzed by the foundational model. Furthermore, note that such boost in performance of the foundational model can be achieved without retraining, fine-tuning, or otherwise altering any of the trainable internal parameters of the foundational model itself.

Now, consider more specifically how the one or more trainable parameters of the pre-processing transformation can be iteratively learned.

In various embodiments, there can be an annotated training dataset corresponding to whatever domain to which the particular medical image belongs. In various aspects, the computerized tool can comprise a training component that can electronically train the pre-processing transformation based on the annotated training dataset.

In various aspects, the annotated training dataset can comprise any suitable number of training medical images, each of which can have the same format, size, or dimensionality as the particular medical image, and each of which can correspond to a respective ground-truth annotation (e.g., to a respective classification label, segmentation mask, or regression output that is known or deemed to be correct or accurate).

In various aspects, prior to beginning training, the training component can randomly initialize the one or more trainable parameters (e.g., the learnable scalar coefficients) of the pre-processing transformation. In contrast, because the foundational model can be already trained, the training component can refrain from re-initializing or otherwise changing any of the trainable internal parameters (e.g., learnable weight matrices, learnable bias values, learnable convolutional kernels) of the foundational model.

In various instances, the training component can select any training medical image and corresponding ground-truth annotation from the annotated training dataset. In various cases, the training component can electronically apply the pre-processing transformation to each pixel (or voxel) of the selected training medical image. In various aspects, such pixel-wise (or voxel-wise) application of the pre-processing transformation can yield a new or adjusted intensity value for each pixel (or voxel) of the selected training medical image. In various instances, such new or adjusted intensity values can collectively be considered as forming an adapted or transformed version of selected training medical image.

Note that the goal of the herein-described training can be for the adapted or transformed version of the selected training medical image to illustrate the same visual content (e.g., anatomical structures) as the selected training medical image but to simultaneously exhibit different visually stylistic characteristics (e.g., contrast, brightness, texture) than the selected training medical image, where such different visually stylistic characteristics are more easily or readily analyzable by the foundational model. Furthermore, note that, if the pre-processing transformation has so far undergone no or little training, then the adapted or transformed version of the selected training medical image can fail to accomplish this goal (e.g., can fail to illustrate the same visual content as the selected training medical image, can fail to exhibit visually stylistic characteristics that are easily or readily analyzable by the foundational model, or can otherwise appear to be visual gibberish).

In various aspects, the training component can execute the foundational model on the adapted or transformed version of the selected training medical image, and such execution can cause the foundational model to produce an output. More specifically, the training component can feed the adapted or transformed version of the selected training medical image to the input layer of the foundational model, the adapted or transformed version of the selected training medical image can complete a forward pass through the one or more hidden layers of the foundational model, and the output layer of the foundational model can compute the output based on activation maps provided by the one or more hidden layers of the foundational model. So, the output can be considered as whatever visual inferencing task result (e.g., as whatever classification label, segmentation mask, or regression output) that the foundational model has predicted for the adapted or transformed version of the selected training medical image.

In various aspects, the training component can compute an error or loss (e.g., mean absolute error (MAE), mean squared error (MSE), cross-entropy error) between the output and the selected ground-truth annotation. In various instances, the training component can incrementally update the one or more trainable parameters of the pre-processing transformation, by performing backpropagation (e.g., stochastic gradient descent) driven by the computed error or loss. In contrast, note that the trainable internal parameters of the foundational model can remain frozen or otherwise unchanged.

In various cases, the training component can repeat the above-described training procedure for any suitable number of training medical images (e.g., for all of the training medical images in the annotated training dataset). This can ultimately cause the computed errors or losses between the outputs produced by the foundational model and available ground-truth annotations to decrease or otherwise become minimized. Such error or loss reduction or minimization can be considered as causing the one or more trainable parameters of the pre-processing transformation to become iteratively optimized for adapting or transforming pixel (or voxel) intensity values to preserve visual content while simultaneously altering or engineering visually stylistic characteristics so as to boost performance of the foundational model. In various aspects, the training component can implement any suitable training batch sizes, any suitable training termination criterion, or any suitable error, loss, or objective function when training the pre-processing transformation in this way.

Note that, because the pre-processing transformation can operate on individual pixels (or voxels) and can have many orders of magnitude fewer trainable parameters than the foundational model, the above-described training of the pre-processing transformation can be significantly less computationally expensive than retraining or fine-tuning of the foundational model would be. Indeed, the pre-processing transformation can be well-trained using many orders of magnitude fewer annotated training medical images, many orders of magnitude fewer training epochs, or many orders of magnitude less training time than would be required to retrain or fine-tune the foundational model. In this way, implementation of the pre-processing transformation as described herein can be considered as a more computationally efficient technique (as compared to retraining or fine-tuning) by which to enable the foundational model to accurately or reliably analyze medical images that it otherwise would not be able to handle.

In various other embodiments, rather than there being the annotated training dataset, there can instead be an auxiliary confidence predictor associated with the foundational model. In various aspects, the training component can electronically train the pre-processing transformation in on-the-fly fashion, based on the auxiliary confidence predictor and based on the particular medical image itself.

In various instances, the auxiliary confidence predictor can be any suitable combination of computer-executable hardware or computer-executable software that can electronically generate a confidence score (e.g., a scalar whose magnitude indicates a level of confidence or certainty) for any given visual inferencing task result produced by the foundational model. In some cases, the auxiliary confidence predictor can be built or otherwise integrated into the foundational model. Indeed, machine learning models are often constructed, trained, or otherwise configured to have primary processing channels (e.g., primary layer stacks) that produce inferencing results and to also have secondary processing channels (e.g., secondary layer stacks) that produce confidence scores associated with those outputted inferencing results. In such situations, the auxiliary confidence predictor can be considered as being whatever secondary processing channel that is included within the foundational model.

But this is a mere non-limiting example. In other cases, the foundational model can lack such a secondary processing channel and can thus refrain from outputting confidence scores. In such situations, the auxiliary confidence predictor can accordingly be a discrete machine learning module that can exhibit any suitable machine learning architecture and that can be separate or distinct from the foundational model. Furthermore, in such situations, the auxiliary confidence predictor can be trained in supervised fashion to receive as input any medical image and any visual inferencing task result corresponding to that medical image, and to produce as output a confidence score for that visual inferencing task result. In various aspects, such supervised training can be facilitated based on the dataset on which the foundational model was originally trained. Indeed, as mentioned above, the dataset on which the foundational model was originally trained can comprise medical images and corresponding ground-truth annotations that represent the correct or accurate visual inferencing task results for respective medical images. In various instances, each image-annotation pair in that dataset can be considered as having a ground-truth confidence score of 100%. So, any trainable internal parameters (e.g., weight matrices, bias values, convolutional kernels) of the auxiliary confidence predictor can be randomly initialized; the auxiliary confidence predictor can be executed on image-annotation pairs selected from that original dataset, thereby yielding inferred confidence scores; errors or losses (e.g., MAE, MSE, cross-entropy) can be computed between such inferred confidence scores and ground-truth confidence scores of 100%; and the trainable internal parameters of the auxiliary confidence predictor can be incrementally updated via backpropagation driven by such computed errors or losses.

In any case, the auxiliary confidence predictor can accurately infer confidence scores for visual inferencing task results produced by the foundational model. In various aspects, the training component can leverage the auxiliary confidence predictor to train the pre-processing transformation in one-the-fly fashion (e.g., when the particular medical image is first encountered and without relying upon annotated images).

In various instances, and as mentioned above, the training component can randomly initialize the one or more trainable parameters of the pre-processing transformation prior to beginning training, and the training component can refrain from re-initializing or otherwise changing any of the trainable internal parameters of the foundational model.

In various aspects, the training component can electronically apply the pre-processing transformation to each pixel (or voxel) of the particular medical image (rather than to an annotated medical image). In various aspects, such pixel-wise (or voxel-wise) application of the pre-processing transformation can yield a new or adjusted intensity value for each pixel (or voxel) of the particular medical image. In various instances, such new or adjusted intensity values can collectively be considered as forming an adapted or transformed version of particular medical image.

As above, the goal of the herein-described training can be for the adapted or transformed version of the particular medical image to illustrate the same visual content (as the particular medical image but to simultaneously exhibit different visually stylistic characteristics than the particular medical image, where such different visually stylistic characteristics are more easily or readily analyzable by the foundational model. Moreover, if the pre-processing transformation has so far undergone no or little training, then the adapted or transformed version of the particular medical image can fail to accomplish this goal.

In various aspects, the training component can execute the foundational model on the adapted or transformed version of the particular medical image, and such execution can cause the foundational model to produce an output. More specifically, the training component can feed the adapted or transformed version of the particular medical image to the input layer of the foundational model, the adapted or transformed version of the particular medical image can complete a forward pass through the one or more hidden layers of the foundational model, and the output layer of the foundational model can compute the output based on activation maps provided by the one or more hidden layers of the foundational model. So, the output can be considered as whatever visual inferencing task result (e.g., as whatever classification label, segmentation mask, or regression output) that the foundational model has predicted for the adapted or transformed version of the particular medical image.

In various aspects, there can be no ground-truth annotation available for the particular medical image. However, training can nevertheless be facilitated. In particular, the auxiliary confidence predictor can generate a confidence score for the output produced by the foundational model, and the training component can incrementally update the one or more trainable parameters of the pre-processing transformation, by performing backpropagation (e.g., stochastic gradient ascent, rather than descent) driven by the confidence score. Just as above, note that the trainable internal parameters of the foundational model can remain frozen or otherwise unchanged.

In various cases, the training component can repeat the above-described training procedure for any suitable number of iterations. This can ultimately cause the confidence scores produced by the auxiliary confidence predictor to increase or otherwise become maximized. Such confidence increase or maximization can be considered as causing the one or more trainable parameters of the pre-processing transformation to become iteratively optimized for adapting or transforming pixel (or voxel) intensity values of the particular medical image to preserve visual content while simultaneously altering or engineering visually stylistic characteristics so as to boost performance of the foundational model. In various aspects, the training component can implement any suitable training termination criterion when training the pre-processing transformation in this way (e.g., can continue training until the most recently-computed confidence score produced by the auxiliary confidence predictor satisfies any suitable threshold).

Again, because the pre-processing transformation can operate on individual pixels (or voxels) and can have many orders of magnitude fewer trainable parameters than the foundational model, the above-described training of the pre-processing transformation can be significantly less computationally expensive than retraining or fine-tuning of the foundational model would be. Indeed, the pre-processing transformation can be well-trained using many orders of magnitude fewer training iterations or many orders of magnitude less training time than would be required to retrain or fine-tune the foundational model. Moreover, when the auxiliary confidence predictor is implemented as described herein, no annotated medical images having similar visually stylistic characteristics as the particular medical image are needed at all. Instead, as described above, the pre-processing transformation can be repeatedly executed on the particular medical image itself until the confidence score computed by the auxiliary confidence predictor is sufficiently high. This can be considered or otherwise referred to as on-the-fly optimization of the pre-processing transformation (e.g., since the pre-processing transformation is being uniquely or specifically optimized for the particular medical image in real-time when the particular medical image is encountered, as opposed to being trained beforehand on annotated medical images). Furthermore, although such embodiments do involve prior training of the auxiliary confidence predictor, such prior training can be considered as de minimus or otherwise not burdensome (e.g., the auxiliary confidence predictor can be trained in conjunction with the foundational model or otherwise on the same already-acquired dataset as the foundational model). Accordingly, implementation of the pre-processing transformation as described herein can be considered as a more computationally efficient technique (as compared to retraining or fine-tuning) by which to enable the foundational model to accurately or reliably analyze medical images that it otherwise would not be able to handle.

Various embodiments described herein can be employed to use hardware or software to solve problems that are highly technical in nature (e.g., to facilitate learnable visual prompt engineering), that are not abstract and that cannot be performed as a set of mental acts by a human. Further, some of the processes performed can be performed by a specialized computer (e.g., deep learning neural networks having internal parameters such as convolutional kernels) for carrying out defined acts related to machine learning.

For example, such defined acts can include: accessing, by a device operatively coupled to a processor, a medical image and a pre-trained machine learning model that is configured to perform a diagnostic or prognostic inferencing task; applying, by the device, a pre-processing transformation to each pixel or voxel of the medical image, thereby yielding a transformed version of the medical image, wherein the pre-processing transformation converts an input pixel or voxel intensity value to an output pixel or voxel intensity value via one or more parameters that are iteratively learned; and performing, by the device, the diagnostic or prognostic inferencing task, by executing the pre-trained machine learning model on the transformed version of the medical image. In some cases, the one or more parameters of the pre-processing transformation can be iteratively learned based on an annotated training dataset. In other cases, the one or more parameters of the pre-processing transformation can be iteratively learned on-the-fly, based on the medical image and based on an auxiliary confidence predictor.

Such defined acts are not performed manually by humans. Indeed, neither the human mind nor a human with pen and paper can: electronically access a medical image (e.g., a pixel array or voxel array captured by a CT scanner or MRI scanner); electronically adapt or transform the medical image via a pixel-wise or voxel-wise pre-processing transformation comprising iteratively learned parameters; and electronically perform a visual inferencing task by executing a pre-trained machine learning model on the adapted or transformed version of the medical image. Indeed, learnable pre-processing transformations and machine learning models are inherently-computerized constructs that simply cannot be meaningfully executed or trained in any way by the human mind without computers. Accordingly, a computerized tool that can adapt a medical image via a pre-processing transformation having iteratively learned parameters and that can execute a pre-trained machine learning model on the adapted version of the medical image is likewise inherently-computerized and cannot be implemented in any sensible, practical, or reasonable way without computers.

Moreover, various embodiments described herein can integrate into a practical application various teachings relating to learnable visual prompt engineering. As explained above, when a foundational model encounters a given medical image that is out-of-domain with respect to the data on which the foundational model was trained, the foundational model cannot accurately or reliably analyze the given medical image. Existing techniques enable the foundational model to accurately or reliably analyze the given medical image by retraining or fine-tuning the foundational model on new annotated medical images that exhibit the same or similar visually stylistic characteristics as the given medical image. Unfortunately, such techniques can be excessively expensive in terms of processing capacity and training time (e.g., the foundational model can comprise millions of trainable internal parameters which can require commensurately voluminous training data and time to fine-tune).

In stark contrast, various embodiments described herein can address one or more of these technical problems. Specifically, a pixel-to-pixel or voxel-to-voxel pre-processing transformation having a small handful (e.g., five or fewer, ten or fewer) of iteratively learned scalar coefficients can be implemented upstream of the foundational model. Such pixel-to-pixel or voxel-to-voxel pre-processing transformation can be trained (e.g., on a small annotated training dataset, or on-the-fly via an auxiliary confidence predictor associated with the foundational model) so as to preserve visual content (e.g., anatomical structures, surgical implants) depicted by the given medical image while adjusting visually stylistic characteristics (e.g., brightness, contrast, texture) of the given medical image, where such adjusting can boost performance of the foundational model. In other words, the pixel-to-pixel or voxel-to-voxel pre-processing transformation, when trained as described herein, can generate an altered or adapted version of the given medical image, where the foundational model is able to accurately or reliably analyze the altered or adapted version of the given medical image. Furthermore, as described herein, the pixel-to-pixel or voxel-to-voxel pre-processing transformation can be implemented without having to retrain, fine-tune, or otherwise modify any of the trainable internal parameters of the foundational model. Further still, because the pixel-to-pixel or voxel-to-voxel pre-processing transformation can have so few trainable parameters (e.g., thousands or millions of times fewer than the foundational model), training of the pixel-to-pixel or voxel-to-voxel pre-processing transformation can consume much less time and much less processing capacity than would retraining or fine-tuning of the foundational model. In other words, various embodiments described herein can enable the foundational model to accurately or reliably analyze medical images that it otherwise would not be able to accurately or reliably analyze, without incurring the excessively high computational costs associated with existing techniques. For at least these reasons, various embodiments described herein are less costly or burdensome than existing techniques and thus certainly constitute a concrete and tangible technical improvement in the field of machine learning. Therefore, various embodiments described herein clearly qualify as useful and practical applications of computers.

Furthermore, various embodiments described herein can control real-world tangible devices based on the disclosed teachings. For example, various embodiments described herein can electronically train or execute real-world deep learning neural networks on real-world medical images (e.g., X-ray scanned images, CT scanned images), and can electronically render on real-world computer screens real-world inferencing task results (e.g., classification labels, segmentation masks, regression results) produced by such real-world deep learning neural networks.

It should be appreciated that the herein figures and description provide non-limiting examples of various embodiments and are not necessarily drawn to scale.

FIG. 1 illustrates a block diagram of an example, non-limiting system 100 that can facilitate learnable visual prompt engineering in accordance with one or more embodiments described herein. As shown, an inferencing task improvement system 102 can be electronically integrated, via any suitable wired or wireless electronic connections, with a pre-trained machine learning model 104 and with a medical image 106.

In various embodiments, the medical image 106 can be any suitable image exhibiting any suitable format, size, or dimensionality. As a non-limiting example, the medical image 106 can be an x-by-y array of pixels, for any suitable positive integers x and y. As another non-limiting example, the medical image 106 can be an x-by-y-by-z array of voxels, for any suitable positive integers x, y, and z. In various aspects, the medical image 106 can visually depict or illustrate any suitable anatomical structures or surgical implants of any suitable medical patient (e.g., human, animal, or otherwise). In various instances, an anatomical structure can be any suitable bodily organ of the medical patient, any suitable bodily tissue of the medical patient, any suitable body part of the medical patient, any suitable bodily fluid of the medical patient, any suitable bodily cavity of the medical patient, or any suitable portion thereof. In various cases, a surgical implant can be any suitable medical hardware (e.g., medical tubing, medical stitches, medical stents, pacemakers, medical rods, medical plates, medical screws) that can be surgically implanted or otherwise inserted into or near any suitable anatomical structure of the medical patient. In various aspects, the medical image 106 can be captured or otherwise generated by any suitable medical imaging modality. As a non-limiting example, the medical image 106 can be captured or generated by a CT scanner, in which case the medical image 106 can be considered as a CT scanned image. As another non-limiting example, the medical image 106 can be captured or generated by an MRI scanner, in which case the medical image 106 can be considered as an MRI scanned image. As yet another non-limiting example, the medical image 106 can be captured or generated by an X-ray scanner, in which case the medical image 106 can be considered as an X-ray scanned image. As even another non-limiting example, the medical image 106 can be captured or generated by an ultrasound scanner, in which case the medical image 106 can be considered as an ultrasound scanned image. As still another non-limiting example, the medical image 106 can be captured or generated by a PET scanner, in which case the medical image 106 can be considered as a PET scanned image. In various instances, the medical image 106 can have undergone any suitable image reconstruction techniques, such as filtered back projection.

In various embodiments, the pre-trained machine learning model 104 can be any suitable machine learning model having or otherwise exhibiting any suitable internal architecture. As a non-limiting example, the pre-trained machine learning model 104 can have or exhibit a deep learning neural network architecture. For instance, the pre-trained machine learning model 104 can have an input layer, one or more hidden layers, and an output layer. In various instances, any of such layers can be coupled together by any suitable interneuron connections or interlayer connections, such as forward connections, skip connections, or recurrent connections. Furthermore, in various cases, any of such layers can be any suitable types of neural network layers having any suitable learnable or trainable internal parameters. For example, any of such input layer, one or more hidden layers, or output layer can be convolutional layers, whose learnable or trainable parameters can be convolutional kernels. As another example, any of such input layer, one or more hidden layers, or output layer can be dense layers, whose learnable or trainable parameters can be weight matrices or bias values. As still another example, any of such input layer, one or more hidden layers, or output layer can be batch normalization layers, whose learnable or trainable parameters can be shift factors or scale factors. Further still, in various cases, any of such layers can be any suitable types of neural network layers having any suitable fixed or non-trainable internal parameters. For example, any of such input layer, one or more hidden layers, or output layer can be non-linearity layers, padding layers, pooling layers, or concatenation layers.

In various aspects, the pre-trained machine learning model 104 can be configured to perform any suitable visual inferencing task on inputted medical images (e.g., images having the same format, size, or dimensionality as the medical image 106). That is, the pre-trained machine learning model 104 can be configured to receive as input any given medical image and to produce as output a visual inferencing task result for that given medical image. In various instances, the format, size, or dimensionality of the visual inferencing task result can depend upon the visual inferencing task that the pre-trained machine learning model 104 is configured to perform. As a non-limiting example, the visual inferencing task can be image classification. In such case, the visual inferencing task result can be a classification label that the pre-trained machine learning model 104 has predicted for the given medical image. As another non-limiting example, the visual inferencing task can be image segmentation. In such case, the visual inferencing task result can be a segmentation mask that the pre-trained machine learning model 104 has predicted for the given medical image. As yet another non-limiting example, the visual inferencing task can be image regression. In such case, the visual inferencing task result can be a regression output (e.g., denoised image, resolution enhanced image, or other continuously-variable output) that the pre-trained machine learning model 104 has predicted for the given medical image. Note that, in various aspects, the visual inferencing task result can be considered as having diagnostic or prognostic relevance with respect to whatever anatomical structures or surgical implants are illustrated in the given medical image.

In various embodiments, the pre-trained machine learning model 104 can be previously trained in supervised fashion on an original training dataset (not shown) to perform the visual inferencing task on inputted medical images. In various aspects, that original training dataset can comprise any suitable number of training images. In various instances, each training image of the original training dataset can have the same format, size, or dimensionality as the medical image 106. As a non-limiting example, suppose that the medical image 106 is an x-by-y pixel array captured or generated by a CT scanner. In such case, each training image in the original training dataset can likewise be an x-by-y pixel array captured or generated by a CT scanner. As another non-limiting example, suppose that the medical image 106 is an x-by-y-by-z voxel array captured or generated by an MRI scanner. In such case, each training image in the original training dataset can likewise be an x-by-y-by-z voxel array captured or generated by an MRI scanner. In various cases, each training image of the original training dataset can correspond to a respective ground-truth annotation. In various aspects, each ground-truth annotation in the original training dataset can be any suitable electronic data that indicates or otherwise represents a correct or accurate visual inferencing task result (e.g., a correct or accurate classification label, a correct or accurate segmentation mask, a correct or accurate regression output) that is known or deemed to correspond to a respective training image in the original training dataset.

Accordingly, the original training dataset can support supervised training of the pre-trained machine learning model 104 (e.g., its trainable internal parameters can be randomly initialized, it can be iteratively executed on the training images in the original training dataset, and its trainable internal parameters can be iteratively updated by backpropagating errors between the outputs it produces during training and the ground-truth annotations in the original training dataset). Such training can involve any suitable error or objective function (e.g., MAE, MSE, cross-entropy), any suitable optimization algorithm (e.g., stochastic gradient descent), any suitable number of training epochs, or any suitable training batch sizes.

However, this is a mere non-limiting example of how the pre-trained machine learning model 104 can be trained. In other cases, the pre-trained machine learning model 104 can instead be trained in unsupervised fashion or in reinforcement learning fashion.

In any case, the medical image 106 can be considered as exhibiting various visually stylistic characteristics. In various aspects, the visually stylistic characteristics of the medical image 106 can encompass any difficult-to-define visual qualities, attributes, or properties of the medical image 106 that materially affect the appearance of the medical image 106 (e.g., that materially affect how the visual content of the medical image 106 appears or looks). Non-limiting examples of such difficult-to-define visual qualities, attributes, or properties can include a visual texture of the medical image 106; a visual contrast of the medical image 106; a visual brightness of the medical image 106; a visual color scheme or shading scheme of the medical image 106; a visual opaqueness, cloudiness, or translucency of the medical image 106; a visual sharpness or resolution of the medical image 106; or other visual patterns by which or through which the medical image 106 depicts, illustrates, or conveys its visual content.

In various cases, the visually stylistic characteristics of the medical image 106 can be subtly or non-subtly different or dissimilar from those on which the pre-trained machine learning model 104 was trained (e.g., different or dissimilar from those of the training images of the original training dataset). Accordingly, the medical image 106 can be considered as being out-of-domain with respect to the original training dataset on which the pre-trained machine learning model 104 was trained. Because the medical image 106 is out-of-domain with respect to the original training dataset, the pre-trained machine learning model 104 can be unable to accurately or reliably perform the visual inferencing task on the medical image 106 (e.g., the medical image 106 can exhibit visually stylistic characteristics that can throw-off/distract the pre-trained machine learning model 104 or against which the pre-trained machine learning model 104 can be considered as not agnostic).

Despite the medical image 106 being out-of-domain for the pre-trained machine learning model 104, it can nevertheless be desired to accurately or reliably perform the visual inferencing task with respect to the visual content of the medical image 106, without retraining or fine-tuning the pre-trained machine learning model 104. As described herein, the inferencing task improvement system 102 can facilitate such performance.

In various embodiments, the inferencing task improvement system 102 can comprise a processor 108 (e.g., computer processing unit, microprocessor) and a non-transitory computer-readable memory 110 that is operably or operatively or communicatively connected or coupled to the processor 108. The non-transitory computer-readable memory 110 can store computer-executable instructions which, upon execution by the processor 108, can cause the processor 108 or other components of the inferencing task improvement system 102 (e.g., access component 112, visual prompt engineering component 114, execution component 116) to perform one or more acts. In various embodiments, the non-transitory computer-readable memory 110 can store computer-executable components (e.g., access component 112, visual prompt engineering component 114, execution component 116), and the processor 108 can execute the computer-executable components.

In various embodiments, the inferencing task improvement system 102 can comprise an access component 112. In various aspects, the access component 112 can electronically receive or otherwise electronically access the pre-trained machine learning model 104 or the medical image 106. In various instances, the access component 112 can electronically retrieve the pre-trained machine learning model 104 or the medical image 106 from any suitable centralized or decentralized data structures (not shown) or from any suitable centralized or decentralized computing devices (not shown). In any case, the access component 112 can electronically obtain or access the pre-trained machine learning model 104 or the medical image 106, such that other components of the inferencing task improvement system 102 can electronically interact with the pre-trained machine learning model 104 or with the medical image 106.

In various embodiments, the inferencing task improvement system 102 can comprise a visual prompt engineering component 114. In various aspects, as described herein, the visual prompt engineering component 114 can electronically generate an adapted or transformed version of the medical image 106, where such adapted or transformed version is more amenable to analysis by the pre-trained machine learning model 104. In various cases, such adaptation or transformation can be accomplished via a pre-processing pixel/voxel transformation that comprises a small handful of iteratively learned parameters.

In various embodiments, the inferencing task improvement system 102 can comprise an execution component 116. In various instances, as described herein, the execution component 116 can electronically execute the pre-trained machine learning model 104 on the adapted or transformed version of the medical image 106, thereby yielding a visual inferencing task result. In various cases, the execution component 116 can electronically transmit the visual inferencing task result to any suitable computing device or can electronically render the visual inferencing task result on any suitable electronic display.

Figure 2:
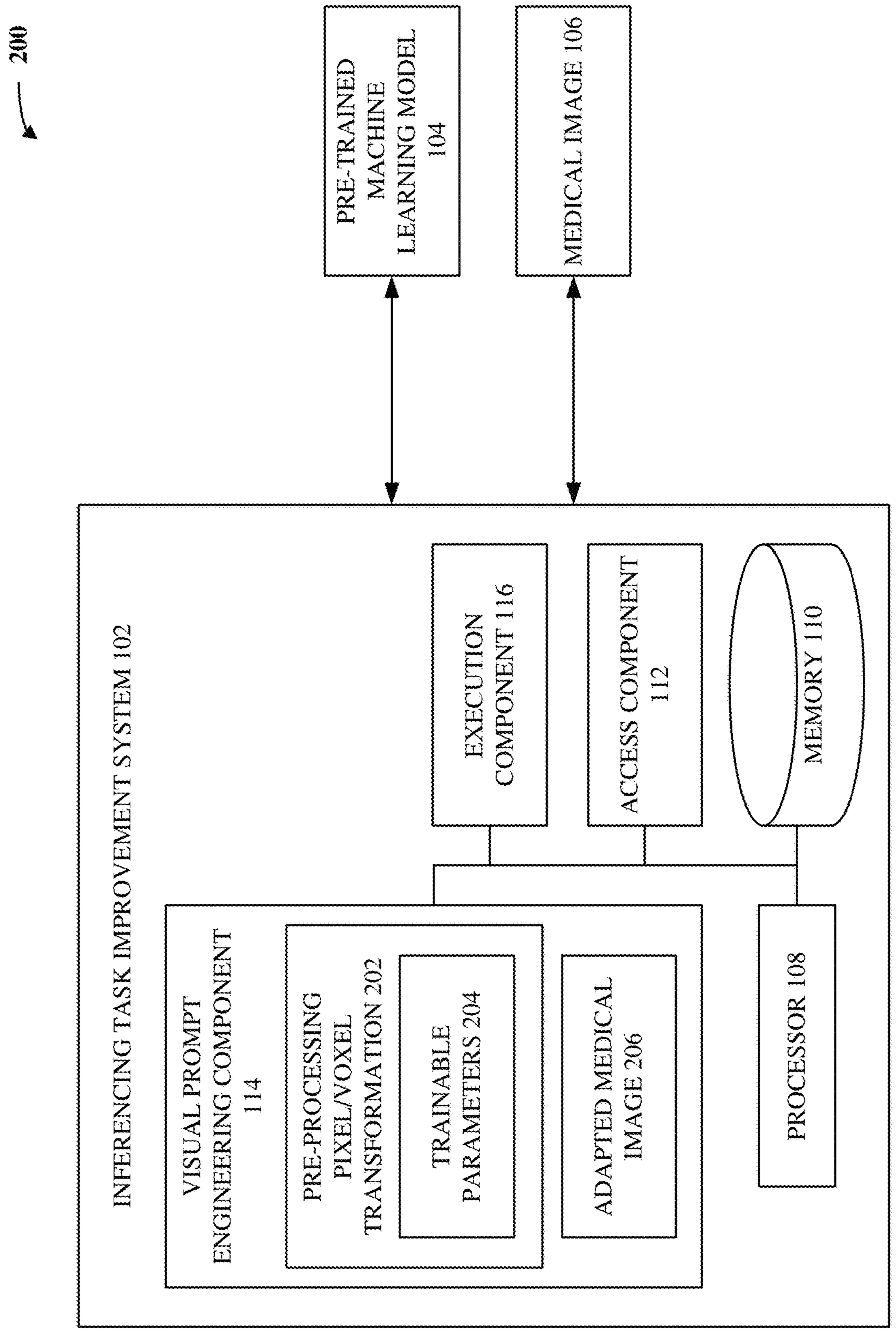
FIG. 2 illustrates a block diagram of an example, non-limiting system including a pre-processing pixel or voxel transformation with trainable parameters that facilitates learnable visual prompt engineering in accordance with one or more embodiments described herein.

FIG. 2 illustrates a block diagram of an example, non-limiting system 200 including a pre-processing pixel or voxel transformation with trainable parameters that can facilitate learnable visual prompt engineering in accordance with one or more embodiments described herein. As shown, the system 200 can, in some cases, comprise the same components as the system 100, and can further comprise a pre-processing pixel/voxel transformation 202 and an adapted medical image 206.

In various embodiments, the visual prompt engineering component 114 can electronically store, electronically maintain, electronically control, or otherwise electronically access the pre-processing pixel/voxel transformation 202. In various aspects, the pre-processing pixel/voxel transformation 202 can be any suitable pixel-to-pixel or voxel-to-voxel function that can comprise a set of trainable parameters 204. In various instances, the visual prompt engineering component 114 can electronically apply the pre-processing pixel/voxel transformation 202 to the medical image 106. In various cases, such application can generate or create the adapted medical image 206. Non-limiting aspects are described with respect to FIG. 3.

Figure 3:
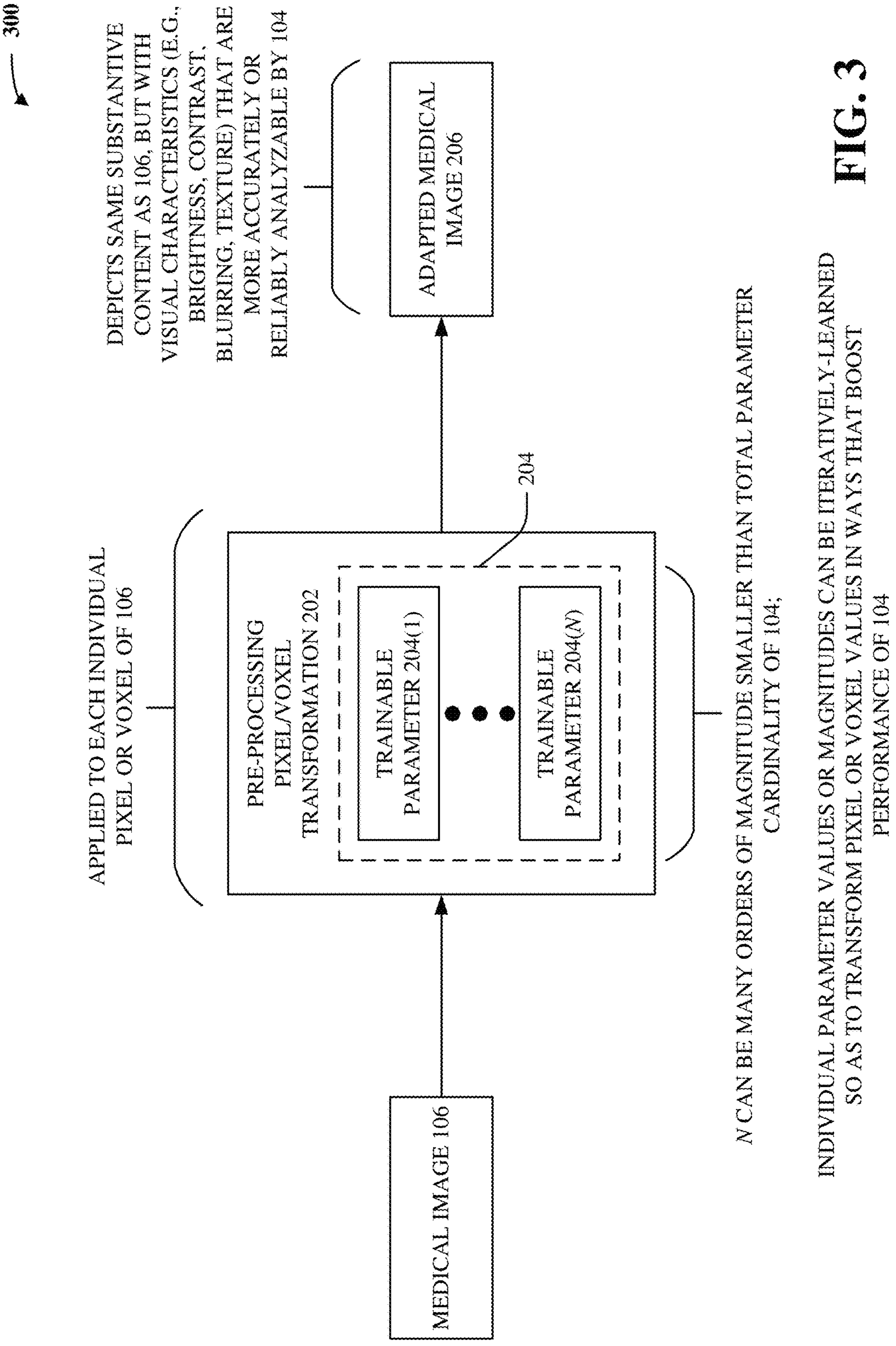
FIG. 3 illustrates an example, non-limiting block diagram showing how a pre-processing pixel or voxel transformation with trainable parameters can adapt or transform a medical image in accordance with one or more embodiments described herein.

FIG. 3 illustrates an example, non-limiting block diagram 300 showing how the pre-processing pixel/voxel transformation 202 can generate the adapted medical image 206 in accordance with one or more embodiments described herein.

In various aspects, the pre-processing pixel/voxel transformation 202 can be any suitable mathematical function that can operate in a pixel-to-pixel (or, equivalently, voxel-to-voxel) fashion. That is, the pre-processing pixel/voxel transformation 202 can be any suitable linear or non-linear mathematical function (e.g., polynomial function, spline function, rational function, root function, exponential function, hyperbolic function, logarithmic function, power function, periodic function, piecewise function, continuous function, discontinuous function, or any suitable combination thereof) that can take as an argument an inputted pixel (or voxel) intensity value, and that can numerically convert that inputted pixel (or voxel) intensity value into an outputted pixel (or voxel) intensity value. In various instances, the pre-processing pixel/voxel transformation 202 can facilitate such numerical conversion via the set of trainable parameters 204. In various cases, the set of trainable parameters 204 can comprise n parameters, for any suitable positive integer n: a trainable parameter 204(1) to a trainable parameter **204(*n*). In various aspects, each of the set of trainable parameters 204 can be a distinct or unique scalar coefficient that can be mathematically applied in any suitable fashion to the inputted pixel (or voxel) intensity value, or to any other of the set of trainable parameters 204. As a non-limiting example, any of the set of trainable parameters 204 can be a distinct or unique scalar coefficient that can be added to or subtracted from the inputted pixel (or voxel) intensity value. As another non-limiting example, any of the set of trainable parameters 204 can be a distinct or unique scalar coefficient that can be multiplied with or divided against the inputted pixel (or voxel) intensity value. As yet another non-limiting example, any of the set of trainable parameters 204 can be a distinct or unique scalar coefficient that can serve as an exponential power or exponential root for the inputted pixel (or voxel) intensity value. As still another non-limiting example, any of the set of trainable parameters 204 can be a distinct or unique scalar coefficient that can serve as an upper bound threshold or a lower bound threshold against which the inputted pixel (or voxel) intensity value can be compared. More generally, any of the set of trainable parameters 204** can be a distinct or unique scalar coefficient that can mathematically interact with the inputted pixel (or voxel) intensity value in any suitable fashion.

In various aspects, the set of trainable parameters 204 can have a small cardinality. Indeed, the set of trainable parameters 204 can have multiple orders of magnitude fewer (e.g., thousands of times fewer, millions of times fewer) trainable parameters than the pre-trained machine learning model 104. For instance, as mentioned above, the pre-trained machine learning model 104 can have millions of trainable internal parameters. The pre-processing pixel/voxel transformation 202, on the other hand, can have five or fewer trainable parameters (e.g., n≤5). This is a mere non-limiting example of n.

In any case, the pre-processing pixel/voxel transformation 202 can be any suitable function or operation that can numerically transform an inputted pixel (or voxel) intensity value into an outputted pixel (or voxel) intensity value via the set of trainable parameters 204.

As a non-limiting example, the pre-processing pixel/voxel transformation 202 can be given by:

$$I_{out} = \frac{I_{in} - a}{\sqrt{1 + (a * (I_{in} - b))^2}}$$

where $I_{in}$ can represent the inputted pixel (or voxel) intensity value, where $I_{out}$ can represent the outputted pixel (or voxel) intensity value, where a can represent a first trainable parameter of the set of trainable parameters 204, and where b can represent a second trainable parameter of the set of trainable parameters 204. In such case, the set of trainable parameters 204 can be considered as having a total cardinality of 2 (e.g., n=2).

As another non-limiting example, the pre-processing pixel/voxel transformation 202 can instead be a color map assignment function that computes the outputted pixel (or voxel) intensity value based on linearly interpolating the inputted pixel (or voxel) intensity value. In various aspects, the color map assignment function can have a first trainable parameter that represents or serves as an intensity window lower-bound, such that any inputted pixel (or voxel) intensity value that is less than or equal to the first trainable parameter can be assigned a minimum color map intensity value as output. In various instances, the color map assignment function can have a second trainable parameter that represents or serves as an intensity window upper-bound, such that any inputted pixel (or voxel) intensity value that is greater than or equal to the second trainable parameter can be assigned a maximum color map intensity value as output. In various cases, any pixel (or voxel) intensity value that is greater than the first trainable parameter but less than the second trainable parameter can be assigned an intermediate color map intensity value as output. In various aspects, such intermediate color map intensity value can be linearly interpolated based on where the inputted pixel (or voxel) intensity value falls in between the first trainable parameter and the second trainable parameter. However, this is a mere non-limiting example. In various instances, the color map assignment function can have a third trainable parameter (e.g., termed a gamma-value) that can represent or serve as an intermediate intensity value checkpoint (e.g., a half-max-output checkpoint, a three-quarter-max output checkpoint, a one-quarter-max output checkpoint), where the third trainable parameter can be greater than the first trainable parameter and less than the second trainable parameter. In various cases, the third trainable parameter can be considered as breaking the intensity window defined by the first and second trainable parameters into two separate linear interpolation regions. In such case, any pixel (or voxel) intensity value that is greater than the first trainable parameter but less than the third trainable parameter can be assigned an intermediate color map intensity value as output that is linearly interpolated based on where the inputted pixel (or voxel) intensity value falls in between the first trainable parameter and the third trainable parameter. Similarly, any pixel (or voxel) intensity value that is greater than the third trainable parameter but less than the second trainable parameter can be assigned an intermediate color map intensity value as output that is linearly interpolated based on where the inputted pixel (or voxel) intensity value falls in between the third trainable parameter and the second trainable parameter. In various cases, multiple gamma-values can be implemented, thereby breaking the intensity window up into even more linear interpolation regions.

In any case, the pre-processing pixel/voxel transformation 202 can convert any given inputted pixel (or voxel) intensity value into an outputted pixel (or voxel) intensity value, based on the set of trainable parameters 204.

In various aspects, the visual prompt engineering component 114 can electronically apply the pre-processing pixel/voxel transformation 202 to each individual pixel (or voxel) of the medical image 106. In other words, the visual prompt engineering component 114 can generate or compute, via the pre-processing pixel/voxel transformation 202, a new intensity value for every single pixel (or voxel) of the medical image 106. In various aspects, such new intensity values can collectively be considered as forming the adapted medical image 206.

As a non-limiting example, suppose that the medical image 106 is an x-by-y pixel array. Consider a pixel (i, j) of the medical image 106, for any suitable positive integers i≤x and j≤y. The pixel (i, j) of the medical image 106 can be considered as having some current or original intensity value. In various aspects, the visual prompt engineering component 114 can feed that current or original intensity value to the pre-processing pixel/voxel transformation 202, and the pre-processing pixel/voxel transformation 202 can compute, based on that current or original intensity value and based on the set of trainable parameters 204, a new or modified intensity value for the pixel (i, j). By repeating this for each pixel of the medical image 106, the visual prompt engineering component 114 can generate a total of x*y new or modified intensity values, each corresponding to a unique, respective pixel location. In various aspects, such total of x*y new or modified intensity values can be considered as collectively forming the adapted medical image 206.

As another non-limiting example, suppose that the medical image 106 is an x-by-y-by-z voxel array. Consider a voxel (i, j, k) of the medical image 106, for any suitable positive integers i≤x, j≤y, and k≤z. The voxel (i, j, k) of the medical image 106 can be considered as having some current or original intensity value. In various aspects, the visual prompt engineering component 114 can feed that current or original intensity value to the pre-processing pixel/voxel transformation 202, and the pre-processing pixel/voxel transformation 202 can compute, based on that current or original intensity value and based on the set of trainable parameters 204, a new or modified intensity value for the voxel (i, j, k). By repeating this for each voxel of the medical image 106, the visual prompt engineering component 114 can generate a total of x*y*z new or modified intensity values, each corresponding to a unique, respective voxel location. In various aspects, such total of x*y*z new or modified intensity values can be considered as collectively forming the adapted medical image 206.

Accordingly, the adapted medical image 206 can have the same format, size, or dimensionality as the medical image 106 (e.g., if the medical image 106 is an x-by-y array of pixels, then the adapted medical image 206 can likewise be an x-by-y array of pixels; if the medical image 106 is an x-by-y-by-z array of voxels, then the adapted medical image 206 can likewise be an x-by-y-by-z array of voxels).

Now, in various aspects, the individual coefficient values or magnitudes of the set of trainable parameters 204 can be iteratively learned, as described further herein, so as to boost performance of the pre-trained machine learning model 104. More specifically, as mentioned above, the medical image 106 can depict or illustrate visual content for which it is desired to perform the visual inferencing task, but the medical image 106 can depict such visual content with visually stylistic characteristics that are not able to be accurately or reliably analyzed by the pre-trained machine learning model 104. In various instances, the individual coefficient values or magnitudes of the set of trainable parameters 204 can be iteratively learned, so as to preserve visual content while simultaneously adjusting visually stylistic characteristics to be more accurately or reliably analyzed by the pre-trained machine learning model 104. Accordingly, due to such iterative learning of the trainable parameters 204, the adapted medical image 206 can be considered as a transformed version of the medical image 106, where such transformed version depicts the same substantive visual content (e.g., same anatomical structures or surgical implants of the same medical patient) as the medical image 106, but where such transformed version depicts such substantive visual content according to different visually stylistic characteristics (e.g., different contrast, different brightness, different texture) that can be more accurately or reliably analyzed by the pre-trained machine learning model 104. In other words, the adapted medical image 206 can be considered as a transformed version of the medical image 106, which transformed version is in-domain with respect to the pre-trained machine learning model 104 was trained.

Figure 4:
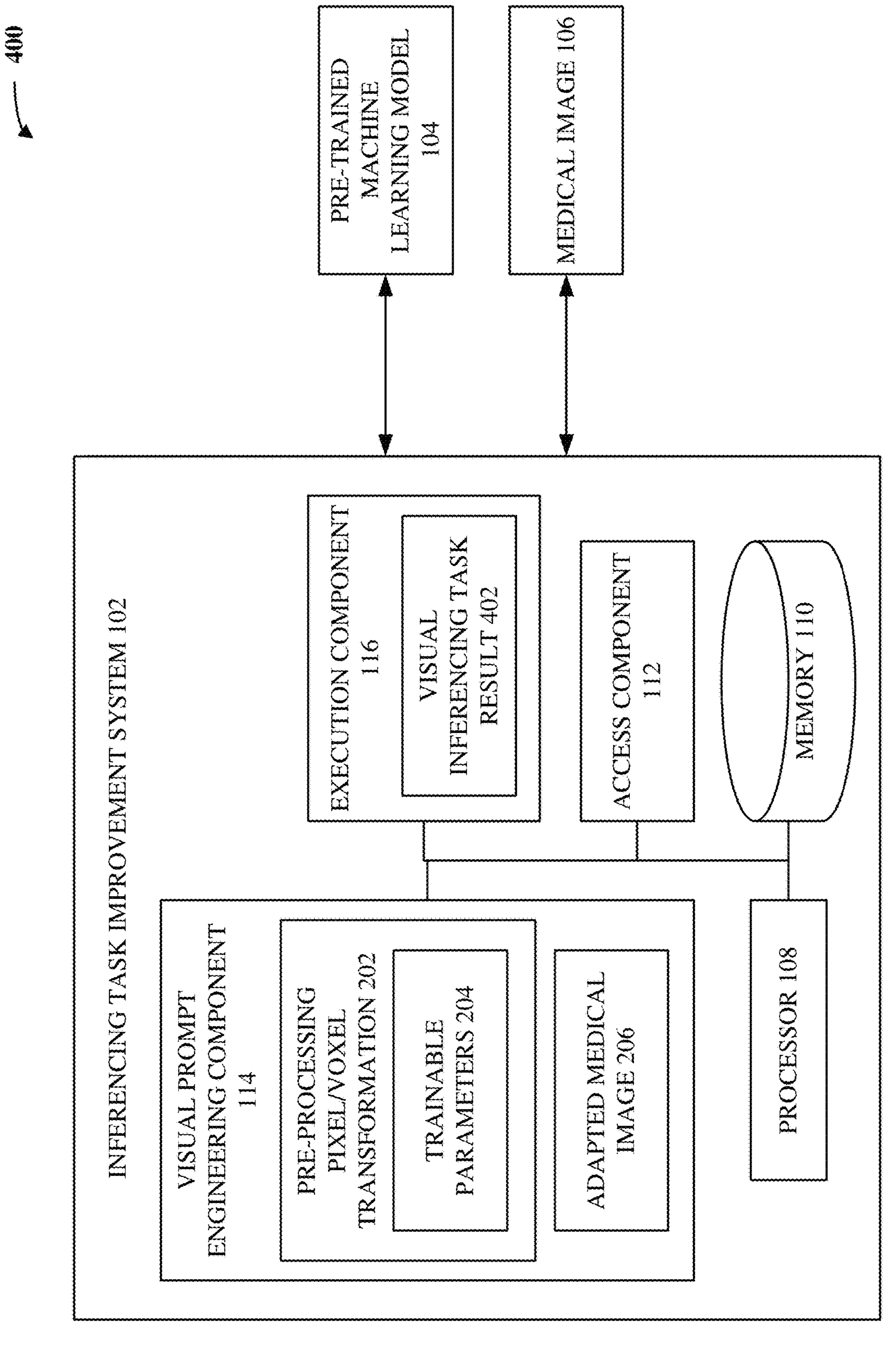
FIG. 4 illustrates a block diagram of an example, non-limiting system including a visual inferencing task result that facilitates learnable visual prompt engineering in accordance with one or more embodiments described herein.

FIG. 4 illustrates a block diagram of an example, non-limiting system 400 including a visual inferencing task result that can facilitate learnable visual prompt engineering in accordance with one or more embodiments described herein. As shown, the system 400 can, in some cases, comprise the same components as the system 200, and can further comprise a visual inferencing task result 402.

In various embodiments, the execution component 116 can electronically generate the visual inferencing task result 402, based on the adapted medical image 206. Non-limiting aspects are described with respect to FIG. 5.

Figure 5:
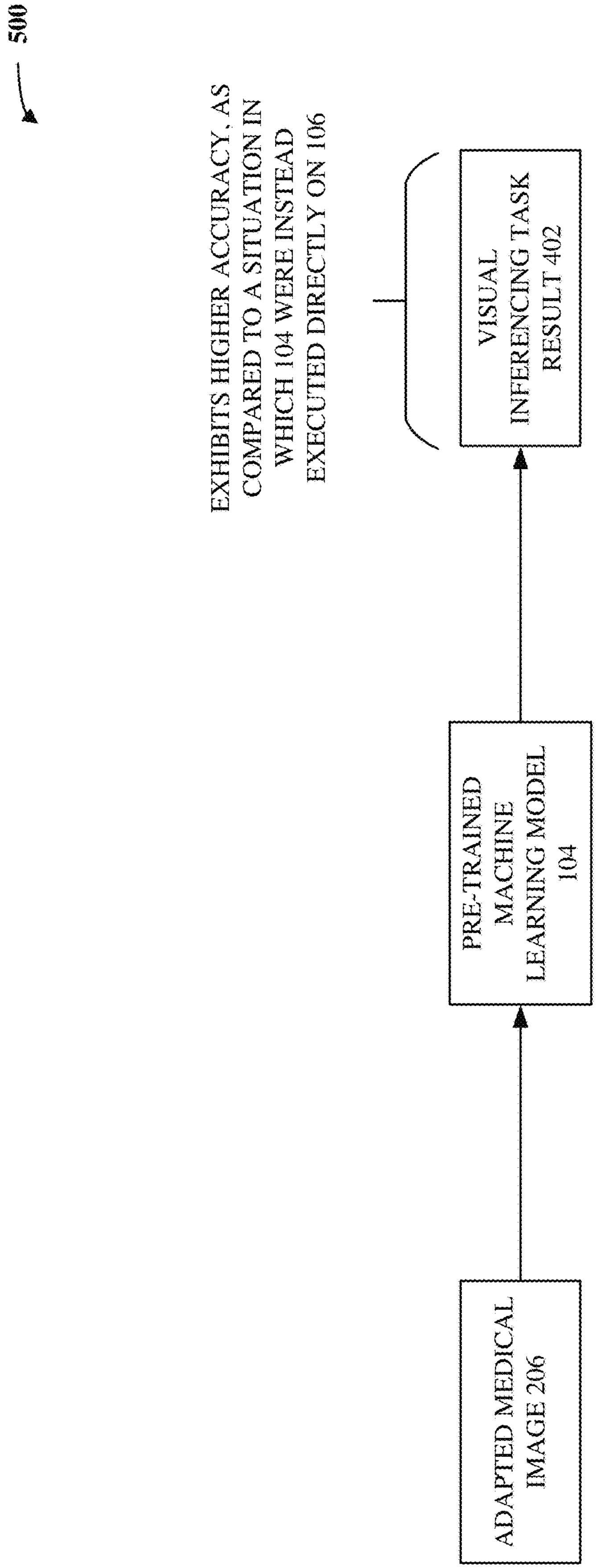
FIG. 5 illustrates an example, non-limiting block diagram showing how a pre-trained machine learning model can generate a visual inferencing task result based on an adapted medical image in accordance with one or more embodiments described herein.

FIG. 5 illustrates an example, non-limiting block diagram 500 showing how the visual inferencing task result 402 can be generated based on the adapted medical image 206 in accordance with one or more embodiments described herein.

In various aspects, the execution component 116 can electronically execute the pre-trained machine learning model 104 on the adapted medical image 206, rather than on the medical image 106. In various instances, such execution can cause the pre-trained machine learning model 104 to produce the visual inferencing task result 402. More specifically, the execution component 116 can feed the adapted medical image 206 to the input layer of the pre-trained machine learning model 104. In various cases, the adapted medical image 206 can complete a forward pass through the one or more hidden layers of the pre-trained machine learning model 104. In various aspects, the output layer of the pre-trained machine learning model 104 can compute or calculate the visual inferencing task result 402 based on activation maps or feature maps produced by the one or more hidden layers of the pre-trained machine learning model 104.

In various aspects, the visual inferencing task result 402 can be any suitable electronic data indicating or representing a result that the pre-trained machine learning model 104 has predicted for the adapted medical image 206 (and thus for medical image 106 by proxy). Accordingly, the format, size, or dimensionality of the visual inferencing task result 402 can depend upon the visual inferencing task that the pre-trained machine learning model 104 is configured to perform. As a non-limiting example, suppose that the visual inferencing task is image classification. In such case, the visual inferencing task result 402 can be a classification label that the pre-trained machine learning model 104 has predicted for the adapted medical image 206, and thus that the pre-trained machine learning model 104 has predicted by proxy for the medical image 106 (e.g., after all, the adapted medical image 206 and the medical image 106 can have the same visual content). As another non-limiting example, suppose that the visual inferencing task is image segmentation. In such case, the visual inferencing task result 402 can be a segmentation mask that the pre-trained machine learning model 104 has predicted for the adapted medical image 206, and thus that the pre-trained machine learning model 104 has predicted by proxy for the medical image 106. As yet another non-limiting example, suppose that the visual inferencing task is image regression. In such case, the visual inferencing task result 402 can be a regression result (e.g., denoised version, modality-transformed version) that the pre-trained machine learning model 104 has predicted for the adapted medical image 206, and thus that the pre-trained machine learning model 104 has predicted by proxy for the medical image 106.

Note that, because the set of trainable parameters 204 can be iteratively learned, as described further herein, to boost performance of the pre-trained machine learning model 104, it can be the case that an accuracy, precision, or reliability of the visual inferencing task result 402 is higher than it would be had the pre-trained machine learning model 104 instead been executed directly on the medical image 106. After all, the medical image 106 can, as explained above, have visually stylistic characteristics that render it out-of-domain with respect to the pre-trained machine learning model 104. In contrast, the adapted medical image 206 can, due to the pre-processing pixel/voxel transformation 202, instead have visually stylistic characteristics that render it in-domain with respect to the pre-trained machine learning model 104. Accordingly, the pre-trained machine learning model 104 can be unable to accurately or reliably perform the visual inferencing task on the medical image 106, but the pre-trained machine learning model 104 can accurately or reliably perform the visual inferencing task on the adapted medical image 206. In this way, the pre-processing pixel/voxel transformation 202 can be considered as improving how the pre-trained machine learning model 104 can perform the visual inferencing task (e.g., as enabling the pre-trained machine learning model 104 to accurately or reliably perform the visual inferencing task on an image that it otherwise would not be able to accurately or reliably analyze). Furthermore, note that such boost in performance can be achieved without retraining, fine-tuning, or otherwise altering the parameters of the pre-trained machine learning model 104 in any way.

In various aspects, the execution component 116 can electronically transmit the visual inferencing task result 402 to any suitable computing device (not shown). In various instances, the execution component 116 can electronically render the visual inferencing task result 402 on any suitable electronic display (e.g., on any suitable computer screen or computer monitor). Accordingly, a user, operator, technician, or medical professional can become aware of the visual inferencing task result 402.

Now, consider more specifically how the set of trainable parameters 204 of the pre-processing pixel/voxel transformation 202 can be iteratively learned. In some cases, the set of trainable parameters 204 can be iteratively learned based on an annotated training dataset, as described with respect to FIGS. 6-8. In other cases, however, the set of trainable parameters 204 can be iteratively learned on-the-fly (e.g., at inferencing time) based on the medical image 106 itself (e.g., not based on an annotated training dataset), as described with respect to FIGS. 9-10.

Figure 6:
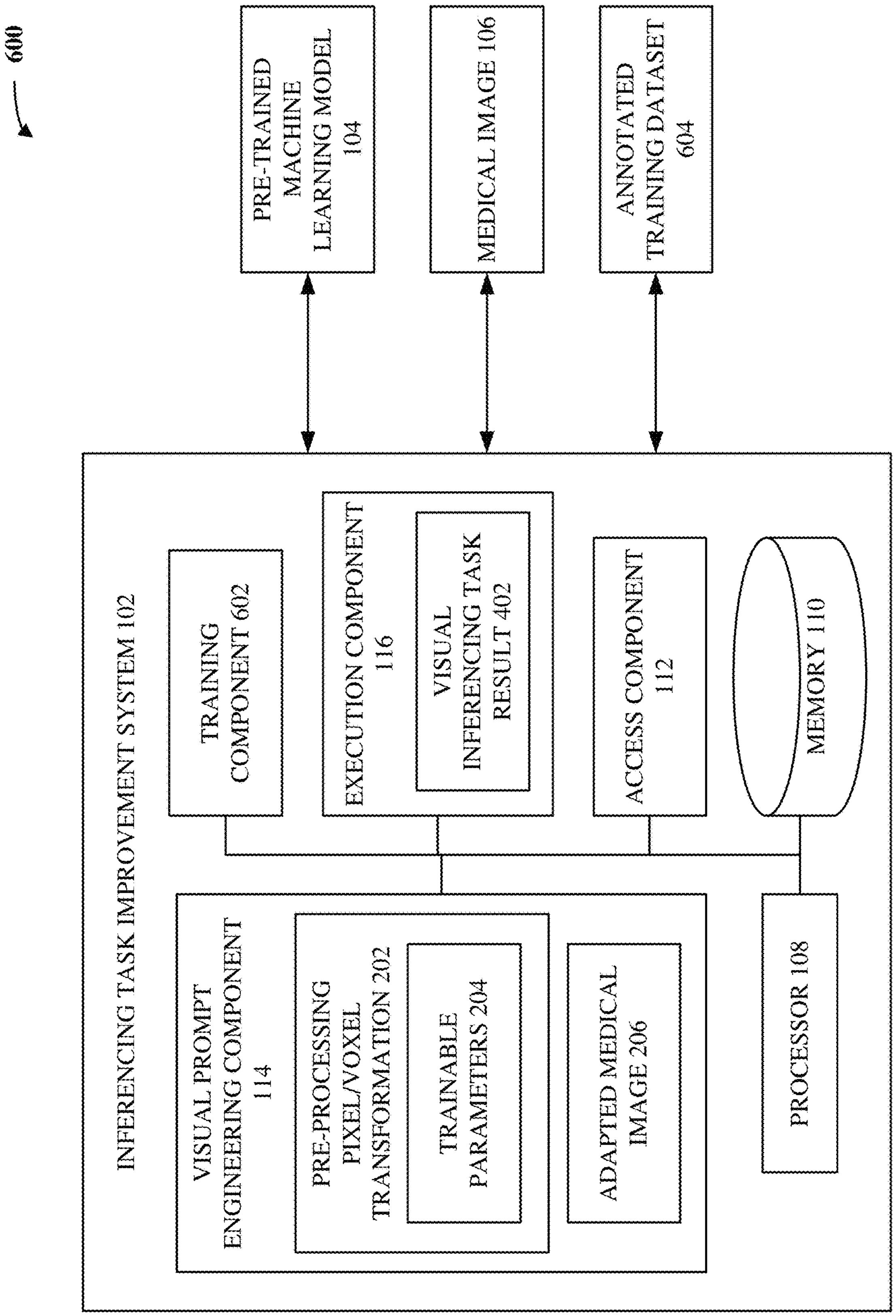
FIG. 6 illustrates a block diagram of an example, non-limiting system including a training component and an annotated training dataset that facilitates learnable visual prompt engineering in accordance with one or more embodiments described herein.
Figure 7:
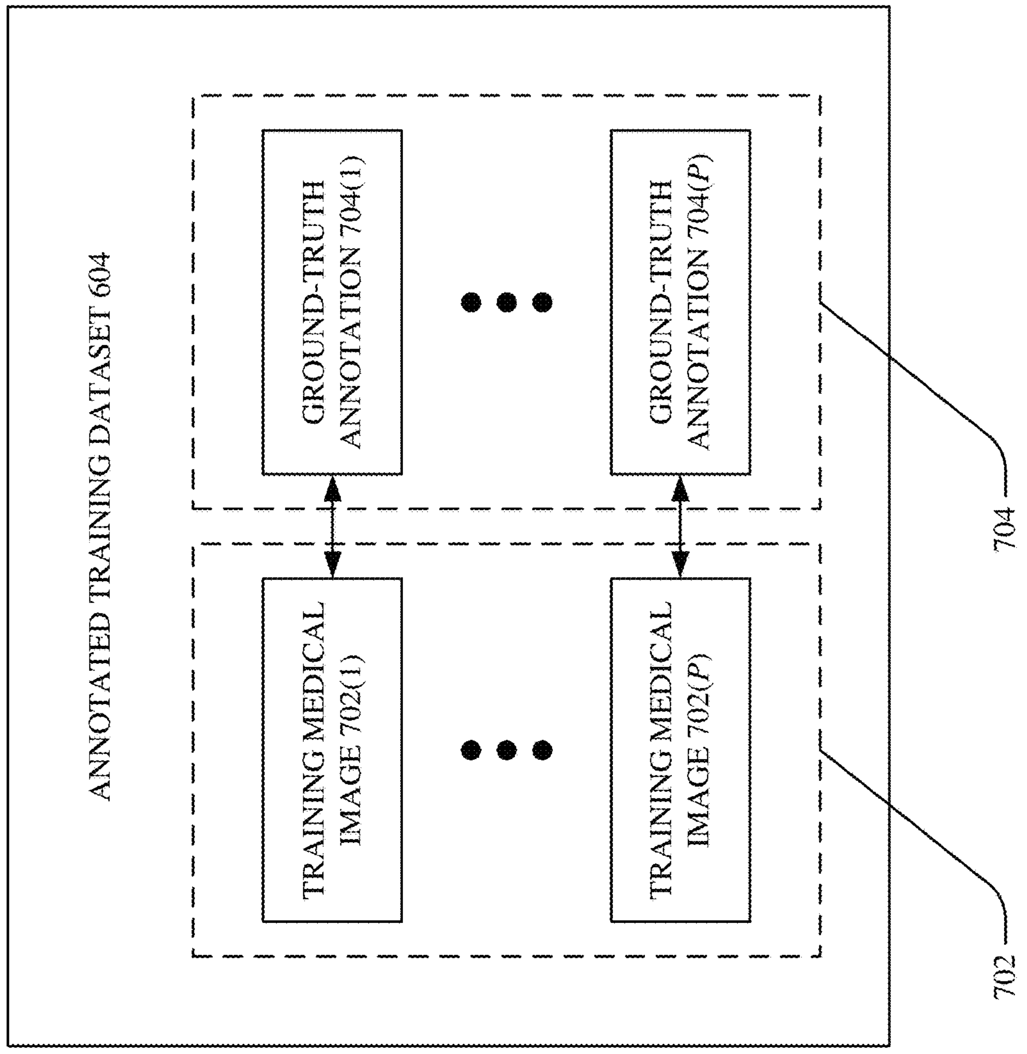
FIG. 7 illustrates an example, non-limiting block diagram of an annotated training dataset in accordance with one or more embodiments described herein.
Figure 8:
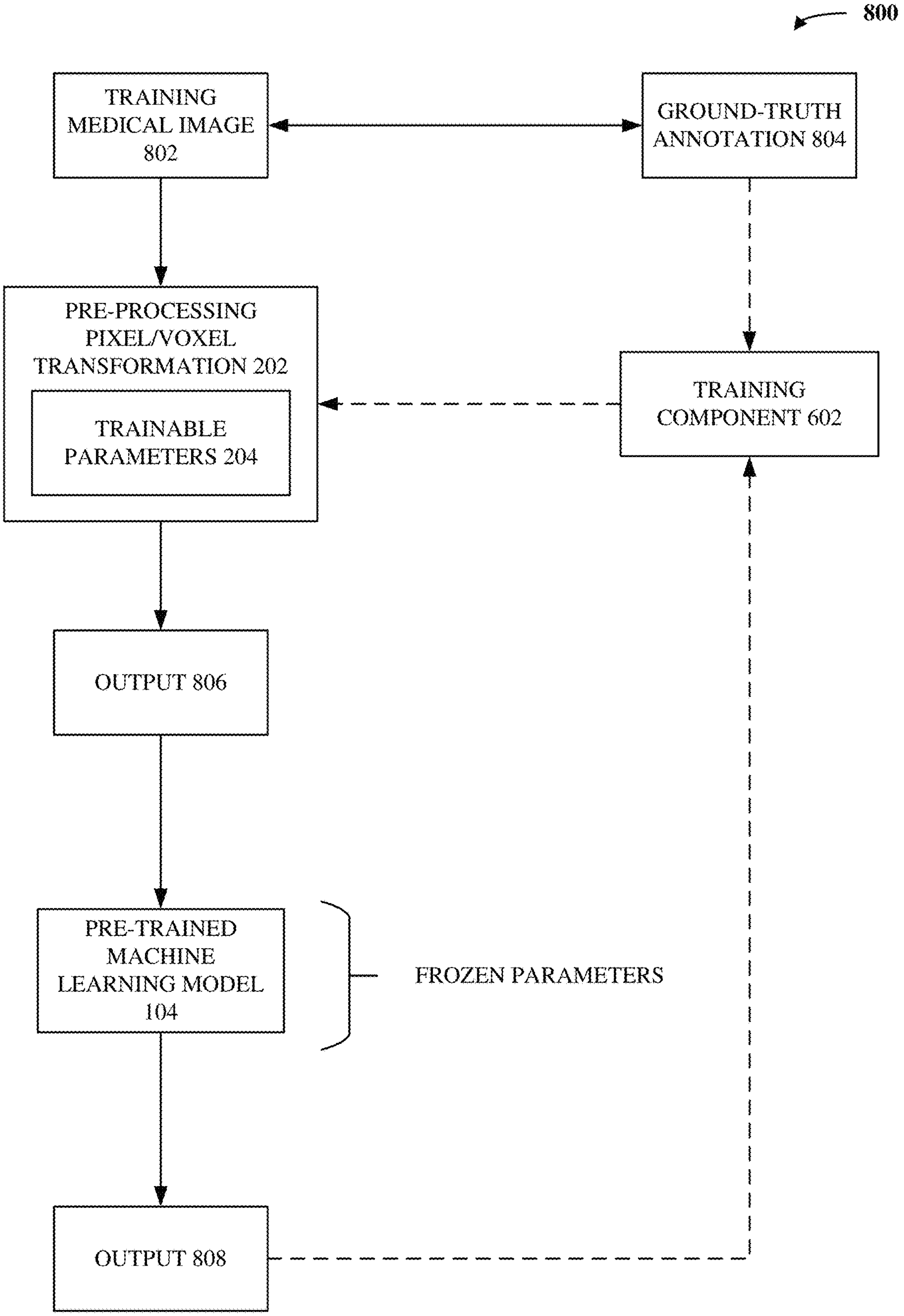
FIG. 8 illustrates an example, non-limiting block diagram showing how trainable parameters of a pre-processing pixel or voxel transformation can be iteratively learned based on an annotated training dataset in accordance with one or more embodiments described herein.

First, consider FIGS. 6-8. FIG. 6 illustrates a block diagram of an example, non-limiting system 600 including a training component and an annotated training dataset that can facilitate learnable visual prompt engineering in accordance with one or more embodiments described herein. As shown, the system 600 can, in some cases, comprise the same components as the system 400, and can further comprise a training component 602 and an annotated training dataset 604.

In various embodiments, the access component 112 can electronically receive, retrieve, or otherwise access, from any suitable source, the annotated training dataset 604. In various aspects, the training component 602 can train the pre-processing pixel/voxel transformation 202 on the annotated training dataset 604. Non-limiting aspects of such training are described with respect to FIGS. 7-8.

FIG. 7 illustrates an example, non-limiting block diagram 700 of the annotated training dataset 604 in accordance with one or more embodiments described herein.

As shown, the annotated training dataset 604 can comprise a set of training medical images 702. In various aspects, the set of training medical images 702 can comprise p images for any suitable positive integer p: a training medical image 702(1) to a training medical image 702(*p*). In various instances, each of the set of training medical images 702 can be a medical image that exhibits the same format, size, or dimensionality as the medical image 106 and that exhibits the same or similar visually stylistic characteristics as the medical image 106. As a non-limiting example, the training medical image 702(1) can be a first medical image depicting some anatomical structure or surgical implant of a first medical patient, having the same number and arrangement of pixels or voxels as the medical image 106, and having the same or similar brightness, contrast, or texture as the medical image 106. As another non-limiting example, the training medical image 702(*p*) can be a p-th medical image depicting some anatomical structure or surgical implant of a p-th medical patient, having the same number and arrangement of pixels or voxels as the medical image 106, and having the same or similar brightness, contrast, or texture as the medical image 106.

In various aspects, as shown, the annotated training dataset 604 can comprise a set of ground-truth annotations 704. In various instances, the set of ground-truth annotations 704 can respectively correspond (e.g., in one-to-one fashion) to the set of training medical images 702. Accordingly, since the set of training medical images 702 can comprise p images, the set of ground-truth annotations 704 can comprise p annotations: a ground-truth annotation 704(1) to a ground-truth annotation 704(*p*). In various cases, each of the set of ground-truth annotations 704 can be considered as a correct or accurate visual inferencing task result that is known or deemed to correspond to a respective one of the set of training medical images 702. As a non-limiting example, the ground-truth annotation 704(1) can correspond to the training medical image 702(1). Accordingly, the ground-truth annotation 704(1) can be considered as being, indicating, or otherwise representing a correct or accurate classification label, segmentation mask, or regression output that is known or deemed to correspond to the training medical image 702(1). As another non-limiting example, the ground-truth annotation 704(*p*) can correspond to the training medical image 702(*p*). So, the ground-truth annotation 704(*p*) can be considered as being, indicating, or otherwise representing a correct or accurate classification label, segmentation mask, or regression output that is known or deemed to correspond to the training medical image 702(*p*).

FIG. 8 illustrates an example, non-limiting block diagram 800 showing how the set of trainable parameters 204 of the pre-processing pixel/voxel transformation 202 can be trained or otherwise iteratively learned based on the annotated training dataset 604 in accordance with one or more embodiments described herein.

In various embodiments, prior to beginning training, the training component 602 can electronically initialize the set of trainable parameters 204 of the pre-processing pixel/voxel transformation 202 in any suitable fashion (e.g., random initialization). However, the training component 602 can refrain from re-initializing or otherwise changing any trainable internal parameters (e.g., weight matrices, bias values, convolutional kernels) of the pre-trained machine learning model 104.

In various aspects, the training component 602 can electronically select any training medical image and corresponding ground-truth annotation from the annotated training dataset 604. These can respectively be referred to as a training medical image 802 and a ground-truth annotation 804.

In various instances, the training component 602 can execute the pre-processing pixel/voxel transformation 202 on each individual pixel (or voxel) of the training medical image 802, thereby yielding an output 806. More specifically, for any given pixel (or voxel) of the training medical image 802, that given pixel (or voxel) can be considered as having a current or original intensity value. In various cases, the training component 602 can feed the current or original intensity value of that given pixel (or voxel) to the pre-processing pixel/voxel transformation 202. In various aspects, the pre-processing pixel/voxel transformation 202 can numerically compute, based on the set of trainable parameters 204 and based on the current or original intensity value of that given pixel (or voxel), a new or resultant intensity value for that given pixel (or voxel). This can be repeated for all of the pixels (or voxels) of the training medical image 802, thereby yielding a plurality of new or resultant intensity values (e.g., one per pixel or per voxel). In various instances, all of such plurality of new or resultant intensity values can collectively be considered as forming the output 806. Thus, the output 806 can be considered as an adapted or transformed version of the training medical image 802.

Note that the goal of training can be for the output 806 to illustrate the same visual content (e.g., same anatomical structures, same surgical implants) as the training medical image 802 but to simultaneously exhibit different visually stylistic characteristics (e.g., contrast, brightness, texture) than the training medical image 802, where such different visually stylistic characteristics are more easily or readily analyzable by the pre-trained machine learning model 104. Moreover, note that, if the pre-processing pixel/voxel transformation 202 has so far undergone no or little training, then the output 806 can fail to accomplish this goal (e.g., can fail to illustrate the same visual content as the training medical image 802, can fail to exhibit visually stylistic characteristics that are easily or readily analyzable by the pre-trained machine learning model 104, or can otherwise appear to be visual gibberish).

In various aspects, the training component 602 can execute the pre-trained machine learning model 104 on the output 806. In various instances, this can cause the pre-trained machine learning model 104 to produce an output 808. More specifically, the training component 602 can feed the output 806 to the input layer of the pre-trained machine learning model 104. In various cases, the output 806 can complete a forward pass through the one or more hidden layers of the pre-trained machine learning model 104. Accordingly, the output layer of the pre-trained machine learning model 104 can compute or calculate the output 808 based on activation maps produced by the one or more hidden layers of the pre-trained machine learning model 104.

Note that the output 808 can be considered as being a predicted visual inferencing task result (e.g., a predicted classification label, a predicted segmentation mask, a predicted regression output) that the pre-trained machine learning model 104 has determined or generated for the output 806. Because the output 806 can be supposed or purported to have the same visual content as the training medical image 802, the output 808 can thus be considered as being the predicted visual inferencing task result that the pre-trained machine learning model 104 has determined by proxy for the training medical image 802. In contrast, the ground-truth annotation 804 can be considered as the correct or accurate visual inferencing task result (e.g., correct or accurate classification label, correct or accurate segmentation mask, correct or accurate regression output) that is known or deemed to correspond to the training medical image 802. Furthermore, again note that, if the pre-processing pixel/voxel transformation 202 has so far undergone no or little training, then the output 806 can fail to be accurately or reliably analyzable by the pre-trained machine learning model 104, which means that the output 808 can be inaccurate or unreliable (e.g., can be significantly different from the ground-truth annotation 804).

In various aspects, the training component 602 can compute an error or loss (e.g., MAE, MSE, cross-entropy) between the output 808 and the ground-truth annotation 804. In various instances, as shown, the training component 602 can incrementally update the set of trainable parameters 204 of the pre-processing pixel/voxel transformation 202, by performing backpropagation (e.g., stochastic gradient descent) driven by the computed error or loss. Note, however, that the trainable internal parameters of the pre-trained machine learning model 104 can be frozen or otherwise unaltered.

In various cases, the training component 602 can repeat the above-described training procedure for any suitable number of training medical images (e.g., for all of the training medical images in the annotated training dataset 604). This can ultimately cause the set of trainable parameters 204 of the pre-processing pixel/voxel transformation 202 to become iteratively optimized for boosting or otherwise improving performance of the pre-trained machine learning model 104. In various aspects, the training component 602 can implement any suitable training batch sizes, any suitable training termination criterion, or any suitable error, loss, or objective function when training the pre-processing pixel/voxel transformation 202.

Note that such training of the pre-processing pixel/voxel transformation 202 can be considered as significantly less computationally expensive than retraining or fine-tuning of the pre-trained machine learning model 104 would be. Indeed, because the pre-processing pixel/voxel transformation 202 can comprise many orders of magnitude fewer trainable parameters than the pre-trained machine learning model 104, it can take much less time, processing capacity, and training data to train the pre-processing pixel/voxel transformation 202 than it would take to effectively retrain or fine-tune the pre-trained machine learning model 104. In other words, since the annotated training dataset 604 is used to train the pre-processing pixel/voxel transformation 202, the size (e.g., p) of the annotated training dataset 604 can be quite small; if the annotated training dataset 604 were instead used to retrain or fine-tune the pre-trained machine learning model 104, the size (e.g., p) of the annotated training dataset 604 would have to be many orders of magnitude larger to effectively accomplish such retraining or fine-tuning.

Figure 9:
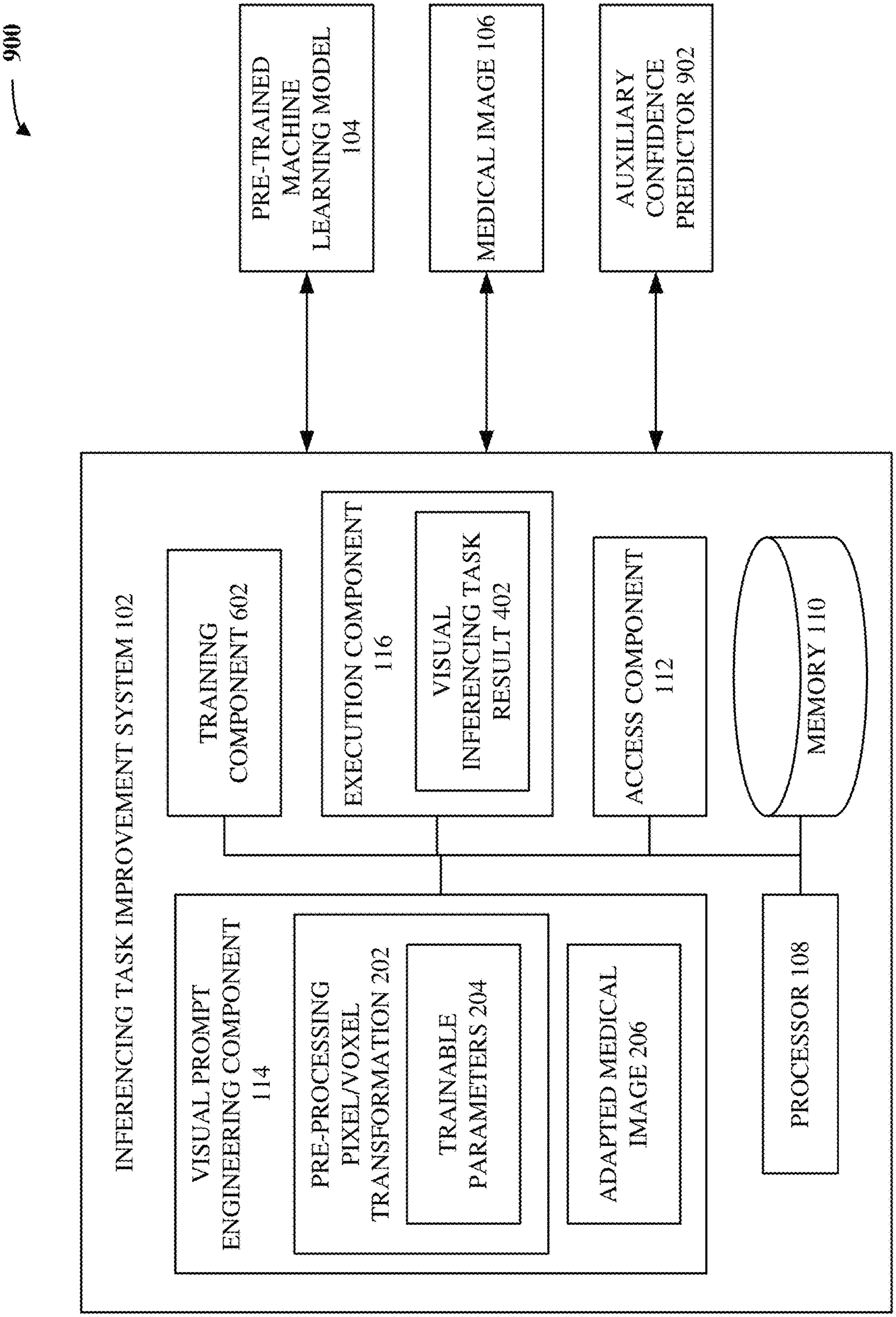
FIG. 9 illustrates a block diagram of an example, non-limiting system including an auxiliary confidence predictor that facilitates learnable visual prompt engineering in accordance with one or more embodiments described herein.
Figure 10:
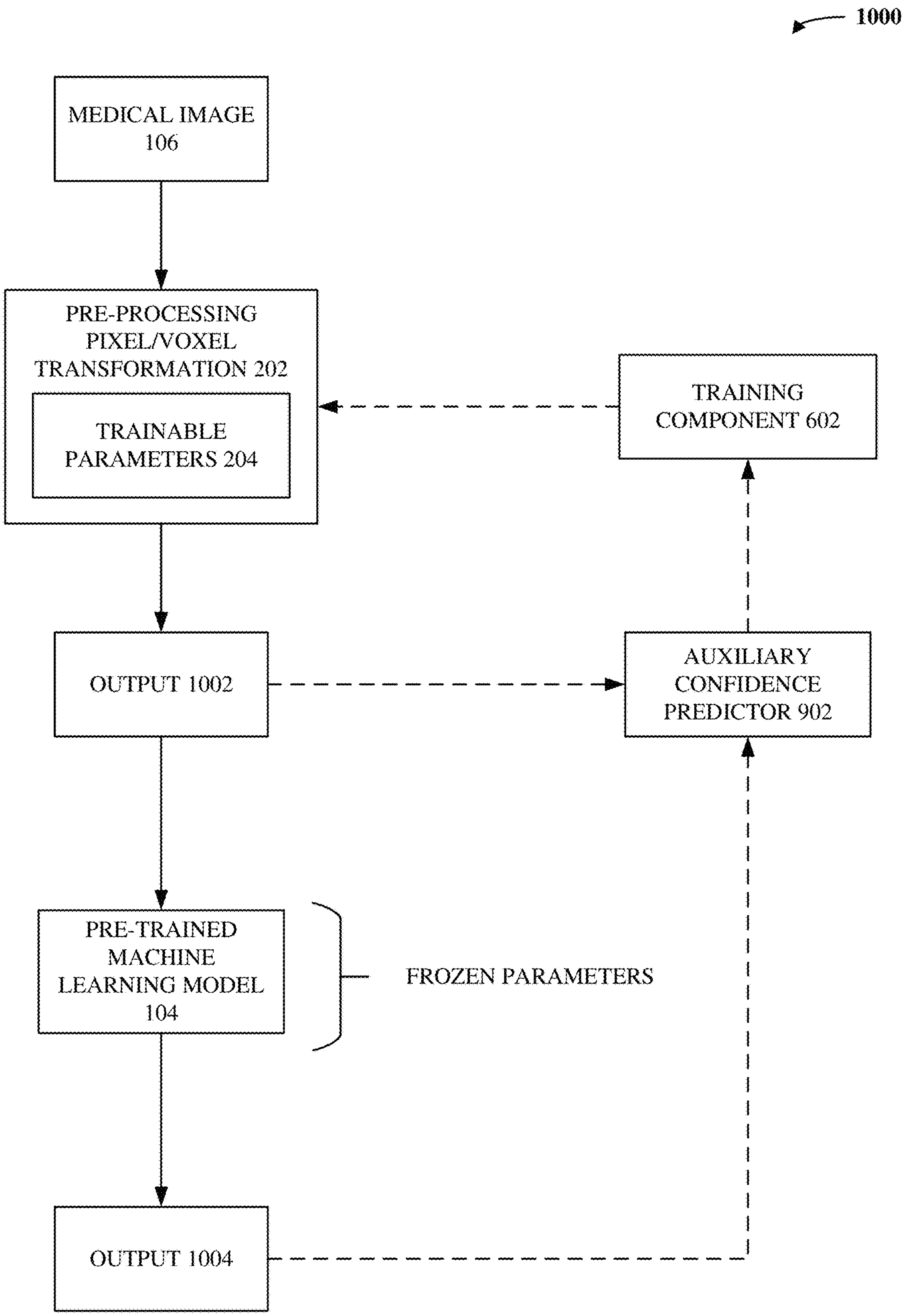
FIG. 10 illustrates an example, non-limiting block diagram showing how trainable parameters of a pre-processing pixel or voxel transformation can be iteratively learned on-the-fly based on an auxiliary confidence predictor in accordance with one or more embodiments described herein.

Now, consider FIGS. 9-10. FIG. 9 illustrates a block diagram of an example, non-limiting system 900 including an auxiliary confidence predictor that can facilitate learnable visual prompt engineering in accordance with one or more embodiments described herein. As shown, the system 900 can, in some cases, comprise the same components as the system 600, and can further comprise an auxiliary confidence predictor 902 instead of the annotated training dataset 604.

In various embodiments, the annotated training dataset 604 can be unavailable. Despite such unavailability, the set of trainable parameters 204 of the pre-processing pixel/voxel transformation 202 can nevertheless be iteratively learned, by leveraging the medical image 106 itself and by leveraging the auxiliary confidence predictor 902.

In various aspects, the auxiliary confidence predictor 902 can be any suitable combination of computer-executable hardware or computer-executable software that can electronically generate, calculate, or otherwise compute a confidence score (e.g., a real-valued scalar ranging from 0 to 1 whose magnitude indicates a level of confidence or certainty) for any visual inferencing task result produced by the pre-trained machine learning model 104.

In some cases, the auxiliary confidence predictor 902 can be built into, integrated into, or otherwise part of the pre-trained machine learning model 104. Indeed, the pre-trained machine learning model 104 can be previously constructed, trained, or otherwise configured to have both a primary processing channel (e.g., a primary stack of neural network layers) and a secondary processing channel (e.g., a secondary stack of neural network layers). In various aspects, the primary processing channel can be responsible for performing the visual inferencing task on inputted medical images, whereas the secondary processing channel can be responsible for estimating confidence scores associated with such performances. In other words, the pre-trained machine learning model 104 can be configured to receive as input any given medical image and to produce as output both a visual inferencing task result (e.g., produced by the primary processing channel) for that given medical image and a confidence score (e.g., produced by the secondary processing channel) for that visual inferencing task result. In such cases, the auxiliary confidence predictor 902 can be considered as being the secondary processing channel that is included within the pre-trained machine learning model 104.

In other cases, however, the pre-trained machine learning model 104 can lack a secondary processing channel and can thus refrain from computing confidence scores. In such situations, the auxiliary confidence predictor 902 can instead be a discrete machine learning module or model that can be separate or distinct from the pre-trained machine learning model 104. In such cases, the auxiliary confidence predictor 902 can exhibit any suitable internal architecture, such as a deep learning neural network architecture. For instance, the auxiliary confidence predictor 902 can have an input layer, one or more hidden layers, and an output layer. In various instances, any of such layers can be coupled together by any suitable interneuron connections or interlayer connections, such as forward connections, skip connections, or recurrent connections. Furthermore, in various cases, any of such layers can be any suitable types of neural network layers having any suitable learnable or trainable internal parameters. For example, any of such input layer, one or more hidden layers, or output layer can be convolutional layers, whose learnable or trainable parameters can be convolutional kernels. As another example, any of such input layer, one or more hidden layers, or output layer can be dense layers, whose learnable or trainable parameters can be weight matrices or bias values. As still another example, any of such input layer, one or more hidden layers, or output layer can be batch normalization layers, whose learnable or trainable parameters can be shift factors or scale factors. Further still, in various cases, any of such layers can be any suitable types of neural network layers having any suitable fixed or non-trainable internal parameters. For example, any of such input layer, one or more hidden layers, or output layer can be non-linearity layers, padding layers, pooling layers, or concatenation layers.

Regardless of its internal architecture in such situations, the auxiliary confidence predictor 902 can be trained in supervised fashion to receive as input any medical image and any visual inferencing task result corresponding to that medical image, and to produce as output a confidence score for that visual inferencing task result. In various aspects, such supervised training can be facilitated based on the original training dataset on which the pre-trained machine learning model 104 was trained (note that such original training dataset is different or distinct from the annotated training dataset 604). As mentioned above, that original training dataset can comprise various medical images (e.g., having visually stylistic characteristics that are different from those of the medical image 106) and corresponding ground-truth annotations that represent the correct or accurate visual inferencing task results for respective ones of those various medical images. In various instances, each image-annotation pair in that original training dataset can be considered as having a ground-truth confidence score of 100% (e.g., a ground-truth confidence score of 1). Thus, the trainable internal parameters (e.g., weight matrices, bias values, convolutional kernels) of the auxiliary confidence predictor 902 can be randomly initialized; the auxiliary confidence predictor 902 can be executed on image-annotation pairs selected from that original training dataset, thereby yielding inferred confidence scores; errors or losses (e.g., MAE, MSE, cross-entropy) can be computed between such inferred confidence scores and ground-truth confidence scores of 100% or 1; and the trainable internal parameters of the auxiliary confidence predictor 902 can be incrementally updated via backpropagation driven by such computed errors or losses.

Regardless of whether the auxiliary confidence predictor 902 is already integrated into the pre-trained machine learning model 104 or is instead separate from the pre-trained machine learning model 104, the auxiliary confidence predictor 902 can accurately infer confidence scores for visual inferencing task results produced by the pre-trained machine learning model 104. In various aspects, the training component 602 can utilize the auxiliary confidence predictor 902 so as to train the pre-processing pixel/voxel transformation 202 in the absence of the annotated training dataset 604. Non-limiting aspects are shown with respect to FIG. 10.

FIG. 10 illustrates an example, non-limiting block diagram 1000 showing how the set of trainable parameters 204 of the pre-processing pixel/voxel transformation 202 can be iteratively learned on-the-fly based on the auxiliary confidence predictor 902 in accordance with one or more embodiments described herein.

In various embodiments, prior to beginning training, the training component 602 can electronically initialize the set of trainable parameters 204 of the pre-processing pixel/voxel transformation 202 in any suitable fashion (e.g., random initialization). However, just like above, the training component 602 can refrain from re-initializing or otherwise changing any trainable internal parameters of the pre-trained machine learning model 104.

In various aspects, the training component 602 can execute the pre-processing pixel/voxel transformation 202 on each individual pixel (or voxel) of the medical image 106, thereby yielding an output 1002. More specifically, for any given pixel (or voxel) of the medical image 106, that given pixel (or voxel) can be considered as having a current or original intensity value. In various cases, the training component 602 can feed the current or original intensity value of that given pixel (or voxel) to the pre-processing pixel/voxel transformation 202. In various aspects, the pre-processing pixel/voxel transformation 202 can numerically compute, based on the set of trainable parameters 204 and based on the current or original intensity value of that given pixel (or voxel), a new or resultant intensity value for that given pixel (or voxel). This can be repeated for all of the pixels (or voxels) of the medical image 106, thereby yielding a plurality of new or resultant intensity values (e.g., one per pixel or per voxel). In various instances, all of such plurality of new or resultant intensity values can collectively be considered as forming the output 1002. Thus, the output 1002 can be considered as an adapted or transformed version of the medical image 106.

Just like above, the goal of training can be for the output 1002 to illustrate the same visual content as the medical image 106 but to simultaneously exhibit different visually stylistic characteristics than the medical image 106, where such different visually stylistic characteristics are more easily or readily analyzable by the pre-trained machine learning model 104. Also just like above, if the pre-processing pixel/voxel transformation 202 has so far undergone no or little training, then the output 1002 can fail to accomplish this goal (e.g., can fail to illustrate the same visual content as the medical image 106, can fail to exhibit visually stylistic characteristics that are easily or readily analyzable by the pre-trained machine learning model 104, or can otherwise appear to be visual gibberish).

In various aspects, the training component 602 can execute the pre-trained machine learning model 104 on the output 1002. In various instances, this can cause the pre-trained machine learning model 104 to produce an output 1004. More specifically, the training component 602 can feed the output 1002 to the input layer of the pre-trained machine learning model 104. In various cases, the output 1002 can complete a forward pass through the one or more hidden layers of the pre-trained machine learning model 104. Accordingly, the output layer of the pre-trained machine learning model 104 can compute or calculate the output 1004 based on activation maps produced by the one or more hidden layers of the pre-trained machine learning model 104.

Note that the output 1004 can be considered as being a predicted visual inferencing task result (e.g., a predicted classification label, a predicted segmentation mask, a predicted regression output) that the pre-trained machine learning model 104 has determined or generated for the output 1002. Because the output 1002 can be supposed or purported to have the same visual content as the medical image 106, the output 1004 can thus be considered as being the predicted visual inferencing task result that the pre-trained machine learning model 104 has determined by proxy for the medical image 106. Furthermore, note that, if the pre-processing pixel/voxel transformation 202 has so far undergone no or little training, then the output 1002 can fail to be accurately or reliably analyzable by the pre-trained machine learning model 104, which means that it can be likely that the output 1004 is inaccurate or unreliable.

Now, in various aspects, the auxiliary confidence predictor 902 can generate a confidence score for the output 1004. In situations where the auxiliary confidence predictor 902 is already built into the pre-trained machine learning model 104, the confidence score can be computed in parallel with the output 1004 by the pre-trained machine learning model 104. In situations where the auxiliary confidence predictor 902 is instead separate from the pre-trained machine learning model 104, the training component 602 can execute the auxiliary confidence predictor 902 on the output 1002 and the output 1004, and such execution can cause the auxiliary confidence predictor 902 to produce the confidence score. More specifically, the training component 602 can feed the output 1002 and the output 1004 to the input layer of the auxiliary confidence predictor 902. In various cases, the output 1002 and the output 1004 can complete a forward pass through the one or more hidden layers of the auxiliary confidence predictor 902. Accordingly, the output layer of the auxiliary confidence predictor 902 can compute or calculate the confidence score based on activation maps produced by the one or more hidden layers of the auxiliary confidence predictor 902.

In various aspects, the training component 602 can incrementally update the set of trainable parameters 204 of the pre-processing pixel/voxel transformation 202, by performing backpropagation driven by the confidence score (e.g., stochastic gradient ascent can be used rather than stochastic gradient descent, since it can be desired to maximize, not minimize, the confidence score). Again, note that the trainable internal parameters of the pre-trained machine learning model 104 can be frozen or otherwise unaltered.

In various cases, the training component 602 can repeat the above-described training procedure for any suitable number of training iterations (e.g., can repeatedly execute the pre-processing pixel/voxel transformation 202 on the medical image 106 and update the set of trainable parameters 204 after each execution). This can ultimately cause the set of trainable parameters 204 of the pre-processing pixel/voxel transformation 202 to become iteratively optimized for boosting performance of the pre-trained machine learning model 104 specifically with respect to the medical image 106 (e.g., such training does not involve annotated images). In various aspects, the training component 602 can implement any suitable training termination criterion when training the pre-processing pixel/voxel transformation 202 in this way. As a non-limiting example, the training component 602 can repeatedly execute the pre-processing pixel/voxel transformation 202 on the medical image 106 and subsequently update the set of trainable parameters 204, until the most recently computed confidence score produced by the auxiliary confidence predictor 902 exceeds any suitable threshold.

Just as above, note that such training of the pre-processing pixel/voxel transformation 202 can be considered as significantly less computationally expensive than retraining or fine-tuning of the pre-trained machine learning model 104 would be. Indeed, because the pre-processing pixel/voxel transformation 202 can comprise many orders of magnitude fewer trainable parameters than the pre-trained machine learning model 104, it can take much less time and processing capacity to train the pre-processing pixel/voxel transformation 202 than it would take to retrain or fine-tune the pre-trained machine learning model 104. Furthermore, when the auxiliary confidence predictor 902 is implemented, the annotated training dataset 604 is not needed at all. Although the auxiliary confidence predictor 902 does require its own training, such training can be considered as not burdensome or expensive. After all, the auxiliary confidence predictor 902 can either: be part of the pre-trained machine learning model 104 itself, in which case it is already trained; or be separately trained on the original training dataset that was used for the pre-trained machine learning model 104, in which case no additional training data acquisition or curation is needed. Further still, note that the training described with respect to FIG. 10 can be considered as being specifically tailored to the medical image 106, as opposed to the training described with respect to FIG. 8 which can be considered as averaged across the annotated training dataset 604. In other words, the training described with respect to FIG. 10 can be considered as optimizing the set of trainable parameters 204 on-the-fly (e.g., at inferencing time without relying on annotated training images) specifically for the medical image 106. Such on-the-fly optimization can be repeated for any given medical image on which it is desired to perform the visual inferencing task.

In any case, implementation of the pre-processing pixel/voxel transformation 202 as described herein can be considered as a computationally inexpensive way to boost performance of the pre-trained machine learning model 104 (e.g., to enable the pre-trained machine learning model 104 to accurately or reliably analyze medical images that it otherwise would not be able to accurately or reliably analyze).

FIGS. 11-20 illustrate example, non-limiting experimental results pertaining to learnable visual prompt engineering in accordance with one or more embodiments described herein.

Figure 11:
FIGS. 11-20 illustrate example, non-limiting experimental results pertaining to learnable visual prompt engineering in accordance with one or more embodiments described herein.
Figure 12:
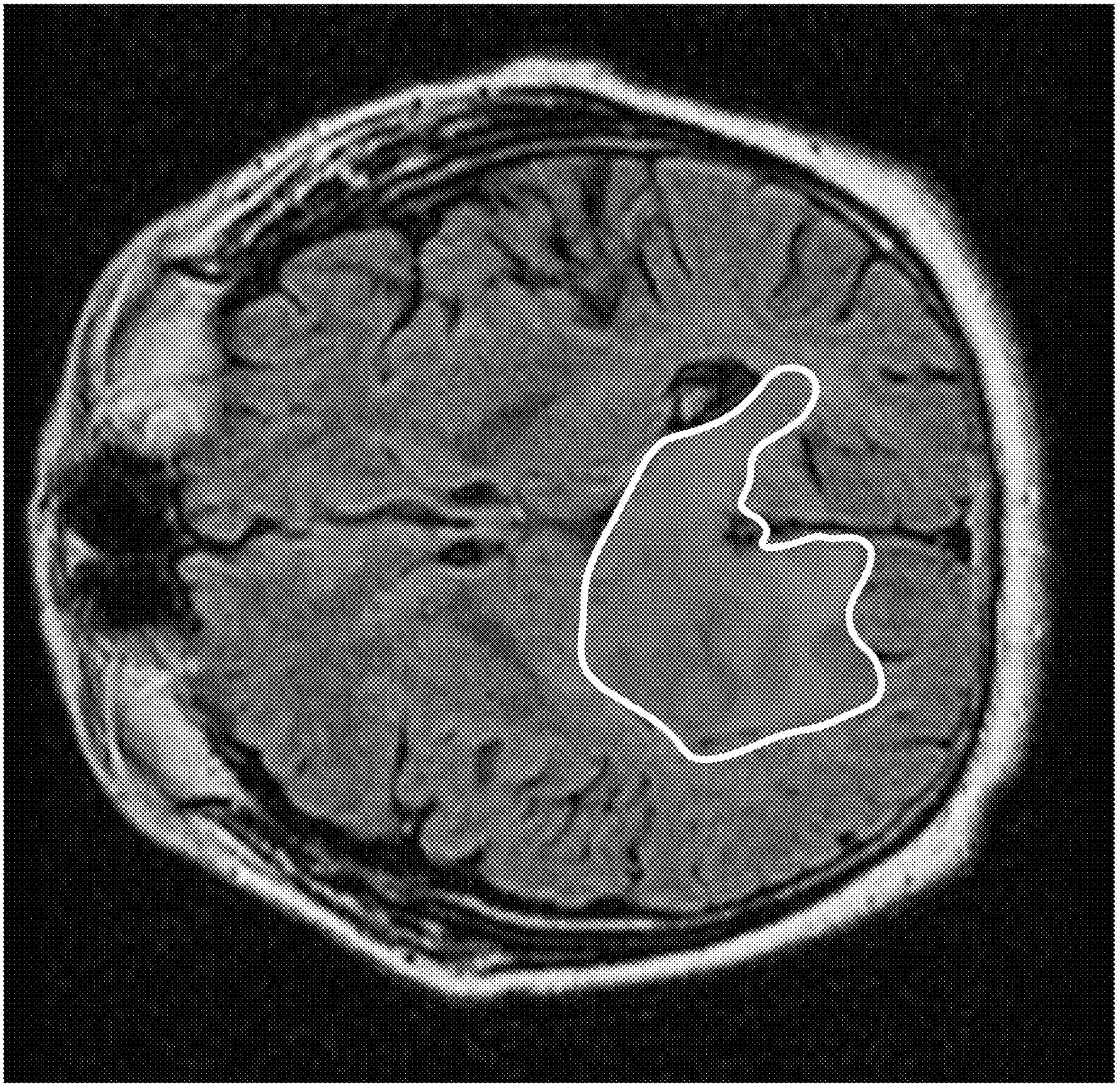

First, consider FIGS. 11-12. In various aspects, the present inventors conducted various experiments in which an embodiment of the inferencing task improvement system 102 was reduced to practice, where the pre-trained machine learning model 104 was configured to perform tumor segmentation on brain images generated by MRI scanners, and where the pre-processing pixel/voxel transformation 202 was given by:

$$I_{out} = \frac{I_{in} - a}{\sqrt{1 + (a * (I_{in} - b))^2}}$$

as described above, where a and b were iteratively learned as described herein.

FIG. 11 illustrates an MRI scanned image 1100 depicting a brain of a medical patient. The pre-trained machine learning model 104 was executed on the MRI scanned image 1100, thereby segmenting a brain tumor of the medical patient. The segmentation produced by the pre-trained machine learning model 104 is visualized by the white boundary in FIG. 11. Such segmentation has a Dice score of 0.75.

FIG. 12 illustrates an adapted MRI image 1200. In various aspects, the adapted MRI image 1200 was produced by pixel-wise application of the pre-processing pixel/voxel transformation 202 to the MRI scanned image 1100. As shown, the adapted MRI image 1200 depicts the same brain of the same medical patient as the MRI scanned image 1100, but the adapted MRI image 1200 exhibits different visually stylistic characteristics (e.g., brightness, contrast, texture) than the MRI scanned image 1100. The pre-trained machine learning model 104 was executed on the adapted MRI image 1200, thereby segmenting the brain tumor of the medical patient. The segmentation produced by the pre-trained machine learning model 104 is visualized by the white boundary in FIG. 12. Such segmentation has a Dice score of 0.86. That is, a significant segmentation accuracy improvement was achieved by implementing the pre-processing pixel/voxel transformation 202 as described herein.

Next, consider FIGS. 13-16. In various aspects, the present inventors conducted various experiments in which an embodiment of the inferencing task improvement system 102 was reduced to practice, where the pre-trained machine learning model 104 was configured to perform tumor segmentation on torso images generated by diffusion-weighted MRI (DW-MRI) scanners, and where the pre-processing pixel/voxel transformation 202 was again given by:

$$I_{out} = \frac{I_{in} - a}{\sqrt{1 + (a * (I_{in} - b))^2}}$$

where a and b were iteratively learned as described herein.

Figure 13:
Figure 14:
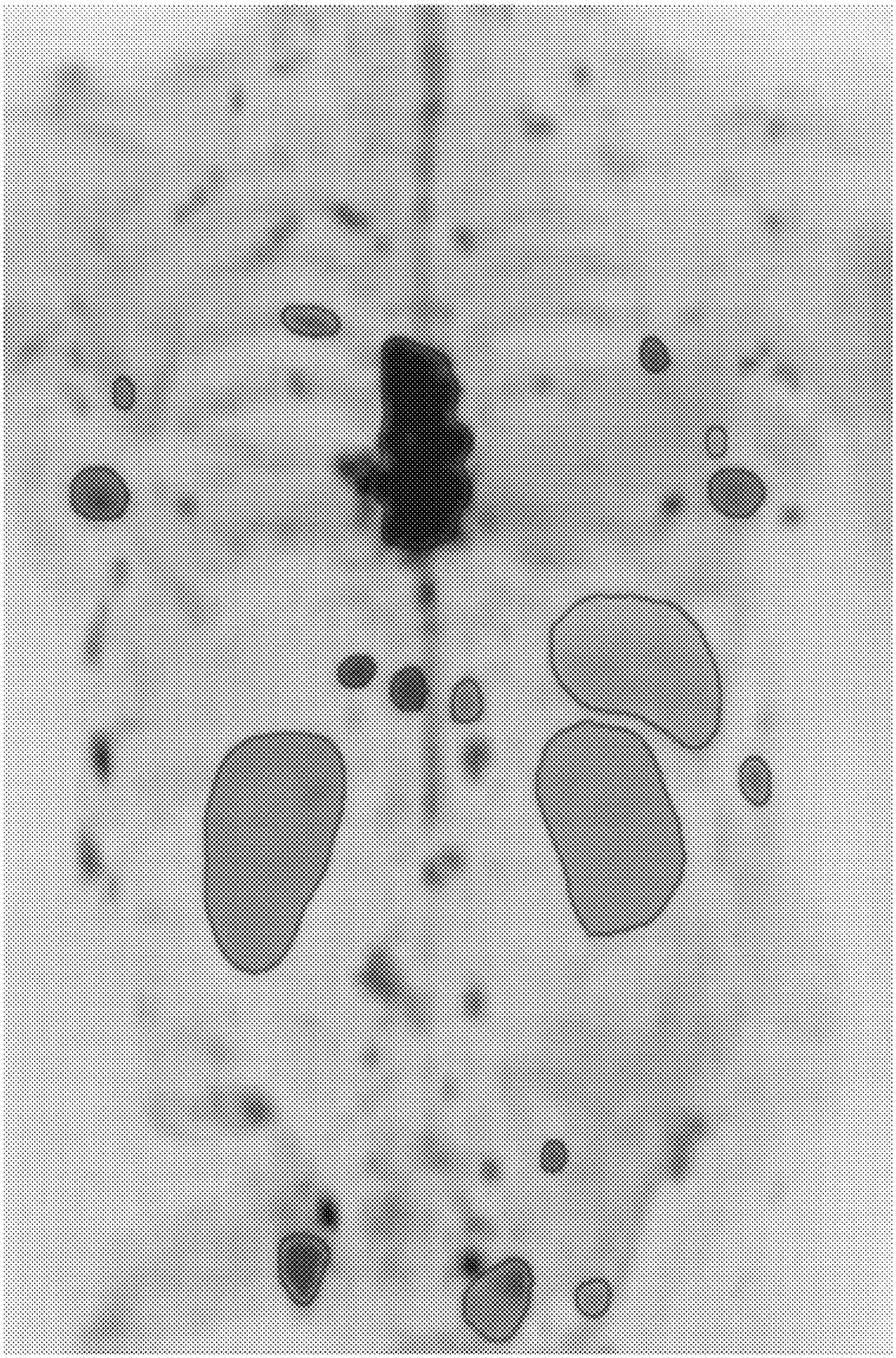

FIG. 13 illustrates a DW-MRI scanned image 1300 depicting a torso of a medical patient. The darker-colored regions in the DW-MRI scanned image 1300 are tumors. As shown, there are very many tumors in the torso of the medical patient.

The pre-trained machine learning model 104 was executed on the DW-MRI scanned image 1300, thereby segmenting whatever torso tumors that it could detect. The segmentations produced by the pre-trained machine learning model 104 are visually demarcated via shaded overlays in FIG. 14, with different shades corresponding to different types, severities, or classes of tumors. As can be seen, the pre-trained machine learning model 104 left very many of the torso tumors depicted in the DW-MRI scanned image 1300 unsegmented.

Figure 15:
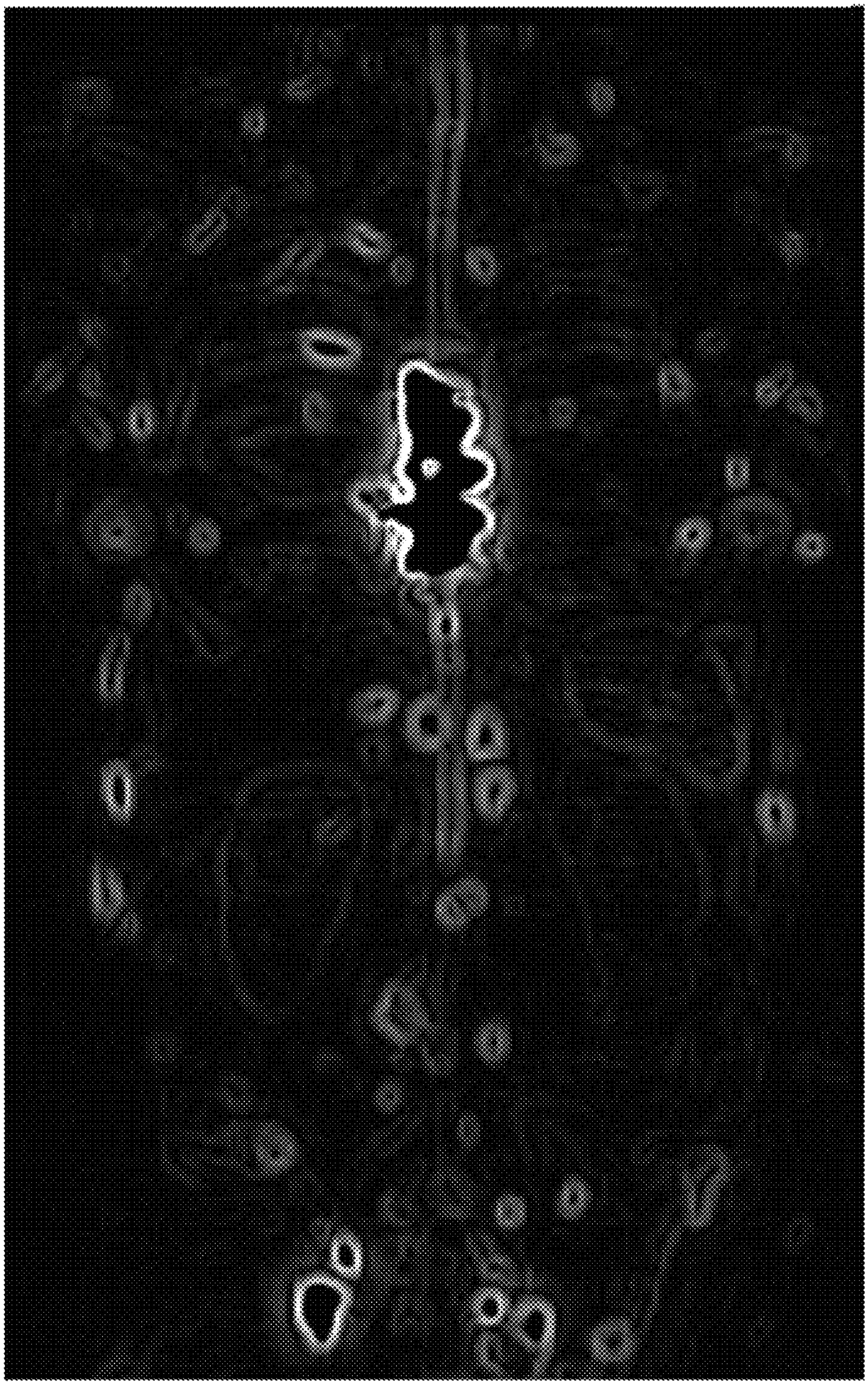
Figure 16:
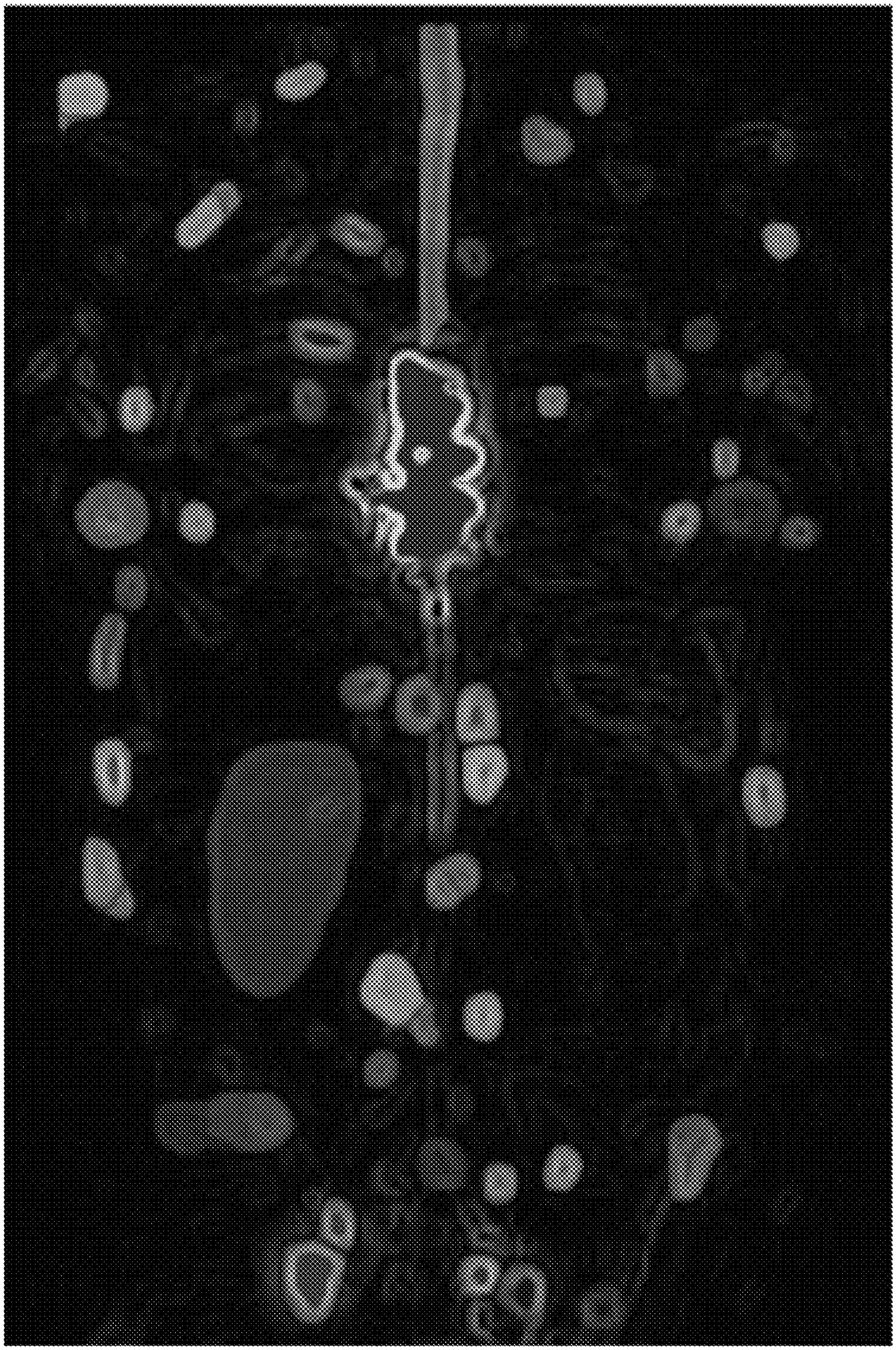

FIG. 15 illustrates an adapted DW-MRI image 1500. In various aspects, the adapted DW-MRI image 1500 was produced by pixel-wise application of the pre-processing pixel/voxel transformation 202 to the DW-MRI scanned image 1300. As shown, the adapted DW-MRI image 1500 depicts the same torso of the same medical patient as the DW-MRI scanned image 1300, but the adapted DW-MRI image 1500 exhibits different visually stylistic characteristics (e.g., brightness, contrast, texture) than the DW-MRI scanned image 1300. Indeed, as shown, the iterative-learning of the pre-processing pixel/voxel transformation 202 caused the adapted DW-MRI image 1500 to be significantly darker overall than the DW-MRI scanned image 1300 and to have visual emphasis applied to the boundaries or edges of torso tumors.

The pre-trained machine learning model 104 was executed on the adapted DW-MRI image 1500, thereby segmenting whatever torso tumors that it could detect. The segmentations produced by the pre-trained machine learning model 104 are visually demarcated via shaded overlays in FIG. 16, again with different shades corresponding to different types, severities, or classes of tumors. As can be seen, the pre-trained machine learning model 104 was able to successfully segment many more torso tumors by being executed on the adapted DW-MRI image 1500, as compared to instead being executed on the DW-MRI scanned image 1300. Again, this shows that a significant segmentation accuracy improvement was achieved by implementing the pre-processing pixel/voxel transformation 202 as described herein.

Now, consider FIGS. 17-20. In various aspects, the present inventors conducted various experiments in which an embodiment of the inferencing task improvement system 102 was reduced to practice, where the pre-trained machine learning model 104 was configured to performed left-lung segmentation on torso images generated by X-ray scanners, and where the pre-processing pixel/voxel transformation 202 was a color map assignment function having three iteratively learned parameters as described above: an intensity window lower bound; an intensity window upper bound; and one gamma-value.

Figure 17:
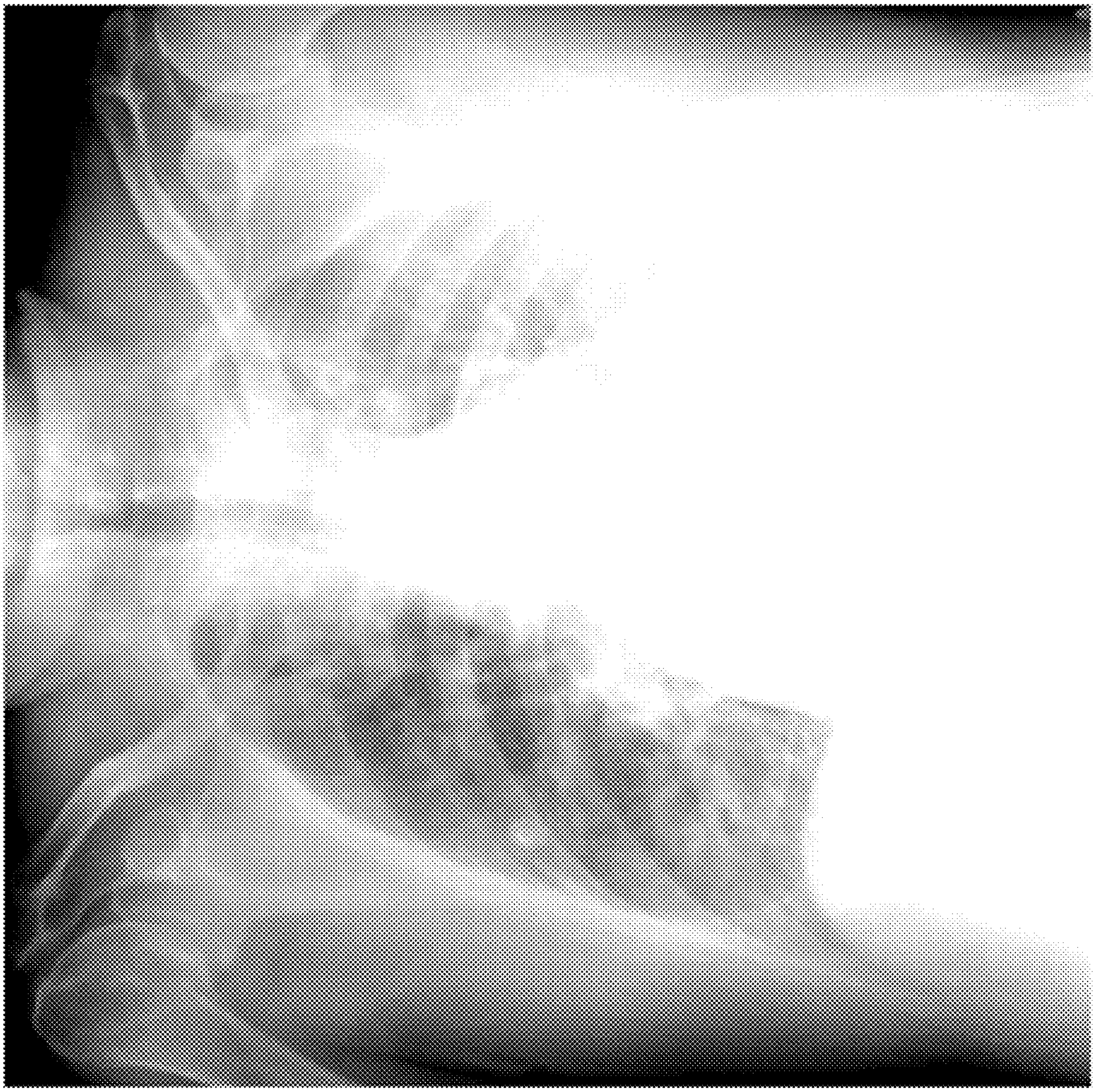
Figure 18:
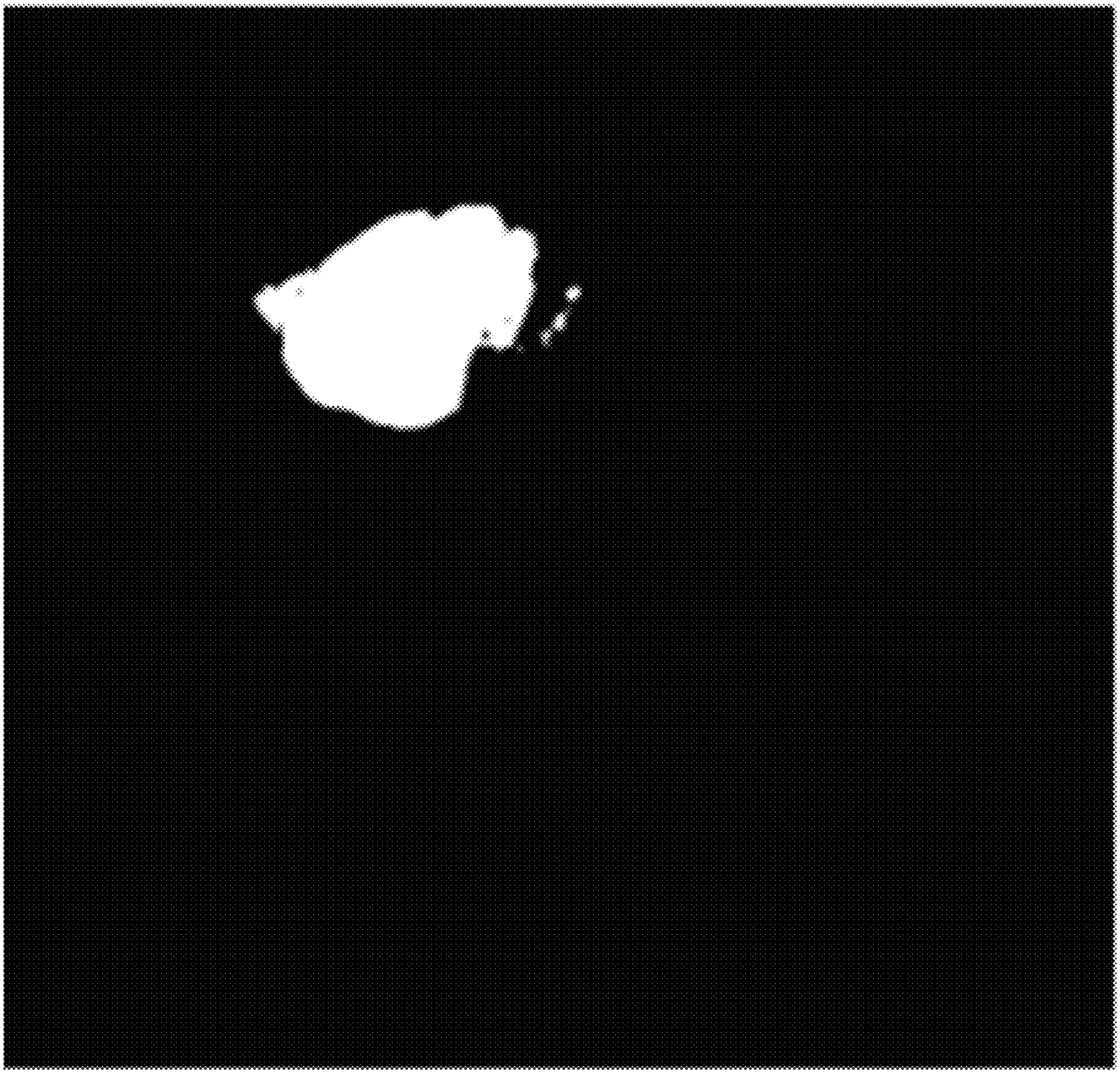

FIG. 17 illustrates an X-ray scanned image 1700 depicting a torso of a medical patient. The pre-trained machine learning model 104 was executed on the X-ray scanned image 1700, thereby yielding a segmentation mask 1800, as shown in FIG. 18. As can be seen in the segmentation mask 1800, the pre-trained machine learning model 104 was able to successfully segment only the top portion or top half of the left lung of the medical patient.

Figure 19:
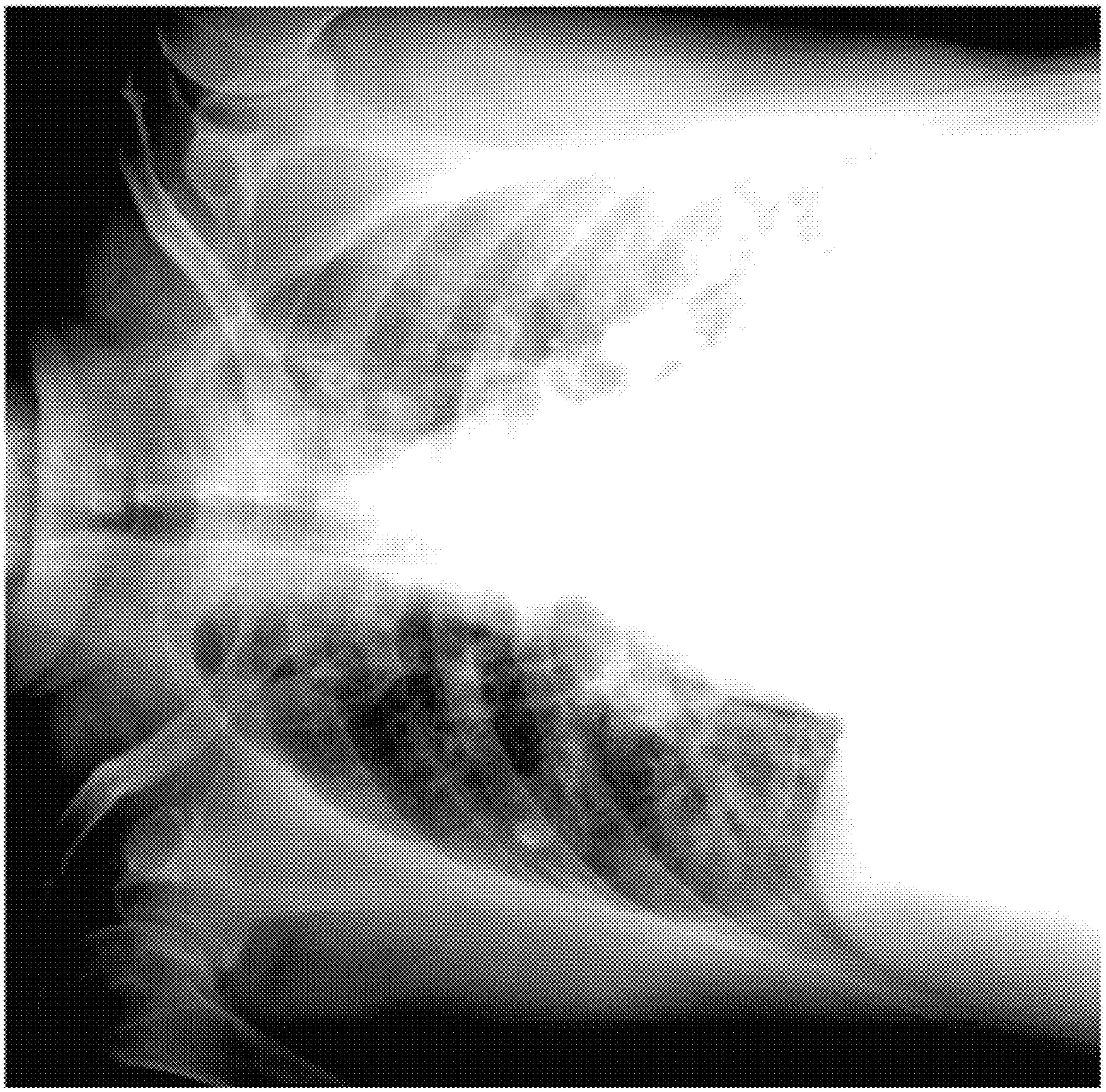
Figure 20:
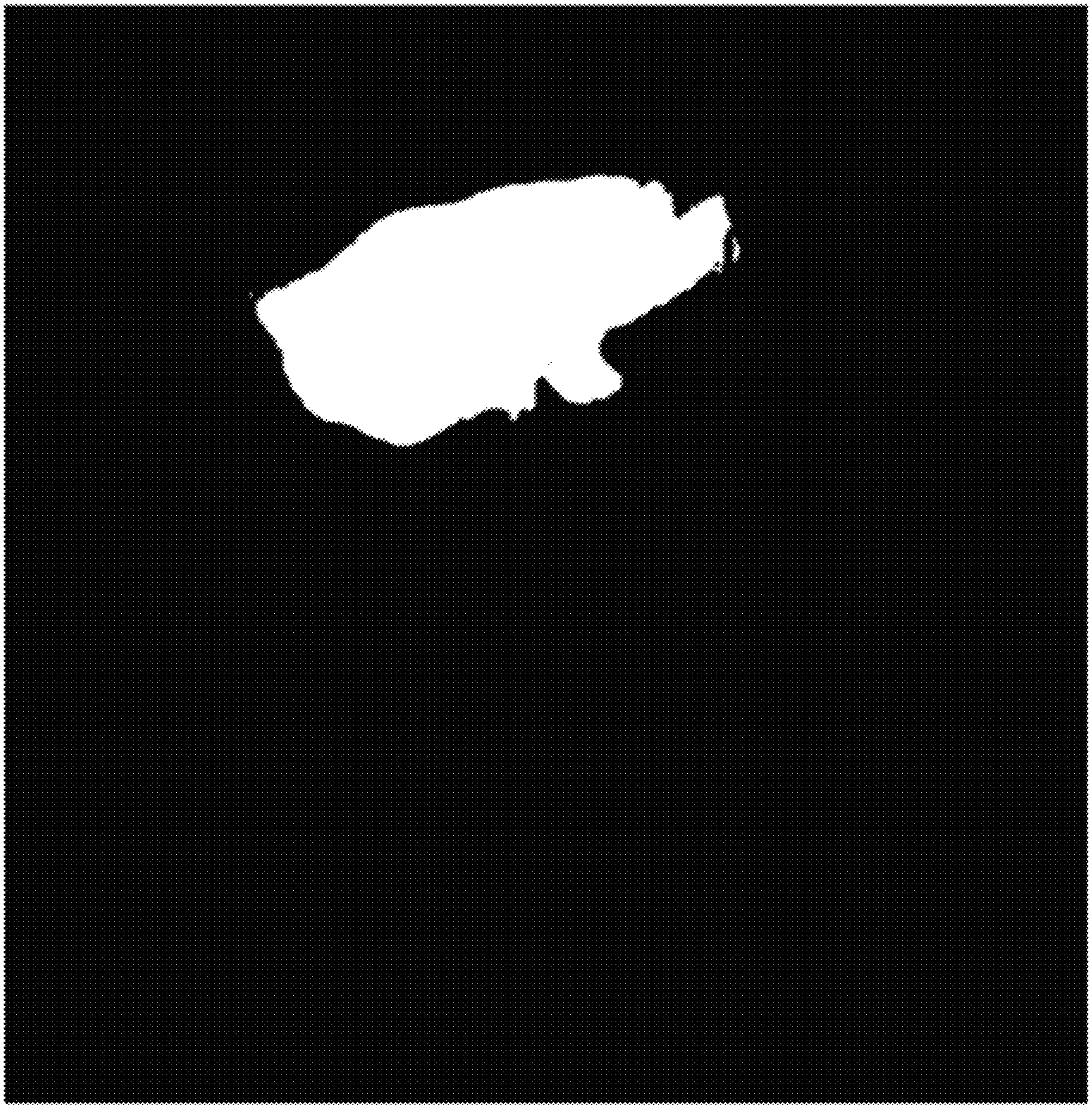

FIG. 19 illustrates an adapted X-ray image 1900. In various aspects, the adapted X-ray image 1900 was produced by pixel-wise application of the pre-processing pixel/voxel transformation 202 to the X-ray scanned image 1700. As shown, the adapted X-ray image 1900 depicts the same torso of the same medical patient as the X-ray scanned image 1700, but the adapted X-ray image 1900 exhibits different visually stylistic characteristics (e.g., brightness, contrast) than the X-ray scanned image 1700. The pre-trained machine learning model 104 was executed on the adapted X-ray image 1900, thereby yielding a segmentation mask 2000, as shown in FIG. 20. As can be seen in the segmentation mask 2000, the pre-trained machine learning model 104 was able to successfully segment much more of the left lung of the medical patient. Again, this shows that a significant segmentation accuracy improvement was achieved by implementing the pre-processing pixel/voxel transformation 202 as described herein.

Although the herein disclosure mainly describes the pre-processing pixel/voxel transformation 202 as being a linear or non-linear function (e.g., polynomial, spline, exponential) or a color map assignment, these are mere non-limiting examples for case of explanation. In other embodiments, the pre-processing pixel/voxel transformation 202 can be any suitable machine learning model (e.g., such as a perceptron or deep learning neural network) that can receive as input a pixel (or voxel) value, and that can numerically transform or convert that inputted pixel (or voxel) value into a new or resultant pixel (or voxel) value.

Figure 21:
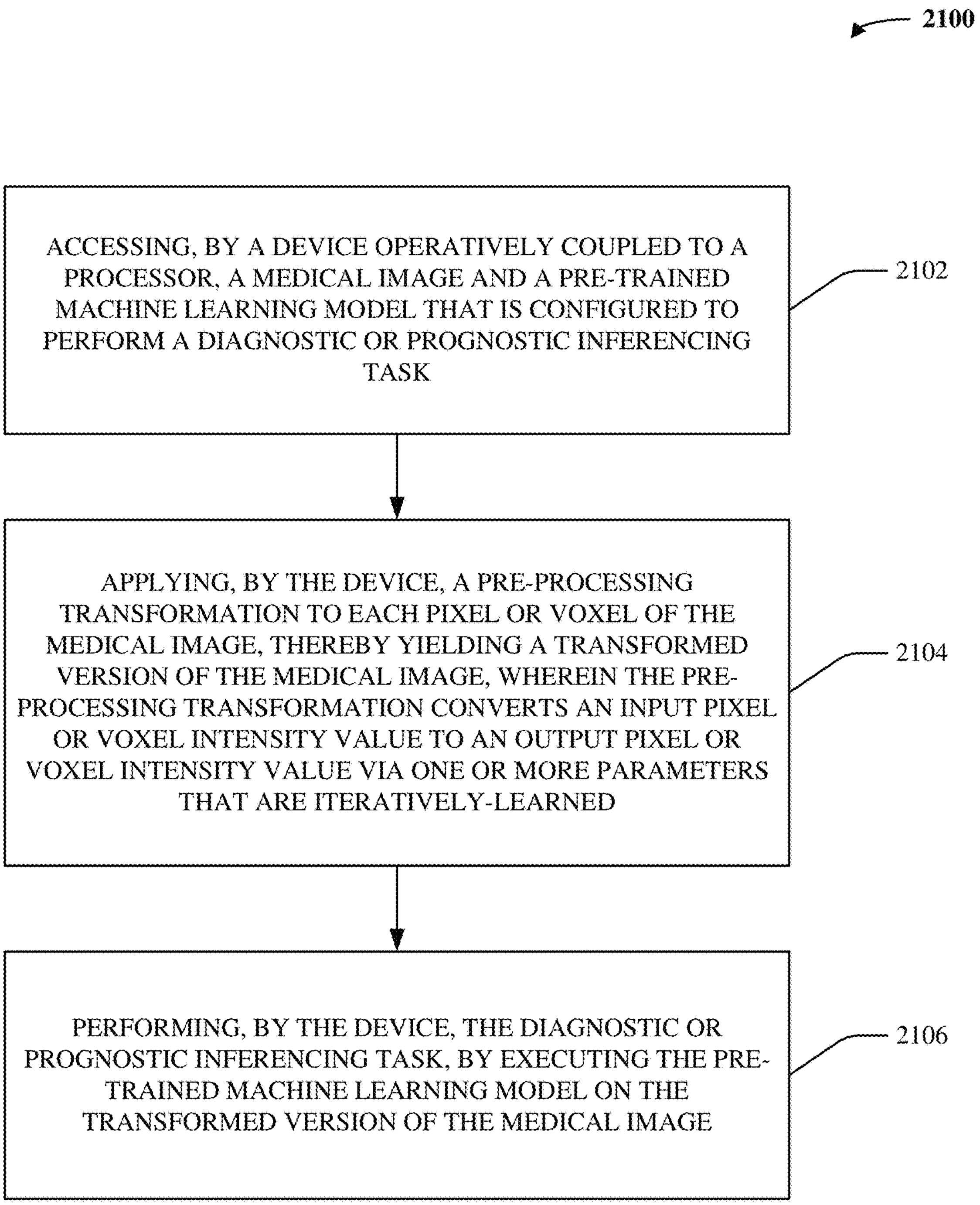
FIG. 21 illustrates a flow diagram of an example, non-limiting computer-implemented method that facilitates learnable visual prompt engineering in accordance with one or more embodiments described herein.

FIG. 21 illustrates a flow diagram of an example, non-limiting computer-implemented method 2100 that can facilitate learnable visual prompt engineering in accordance with one or more embodiments described herein. In various cases, the inferencing task improvement system 102 can facilitate the computer-implemented method 2100.

In various embodiments, act 2102 can include accessing, by a device (e.g., via 112) operatively coupled to a processor (e.g., 108), a medical image (e.g., 106) and a pre-trained machine learning model (e.g., 104) that is configured to perform a diagnostic or prognostic inferencing task.

In various aspects, act 2104 can include applying, by the device (e.g., via 114), a pre-processing transformation (e.g., 202) to each pixel or voxel of the medical image, thereby yielding a transformed version (e.g., 206) of the medical image, wherein the pre-processing transformation converts an input pixel or voxel intensity value to an output pixel or voxel intensity value via one or more parameters (e.g., 204) that are iteratively learned.

In various instances, act 2106 can include performing, by the device (e.g., via 116), the diagnostic or prognostic inferencing task, by executing the pre-trained machine learning model on the transformed version of the medical image.

Although not explicitly shown in FIG. 21, the one or more parameters of the pre-processing transformation can be iteratively learned based on an annotated training dataset (e.g., 604). In particular, the annotated training dataset can comprise a training medical image (e.g., 802) corresponding to a ground-truth annotation (e.g., 804), and the computer-implemented method 2100 can further comprise: randomly initializing, by the device (e.g., via 602), the one or more parameters of the pre-processing transformation; executing, by the device (e.g., via 602), the pre-processing transformation on the training medical image, thereby yielding a first output (e.g., 806); executing, by the device (e.g., 602), the pre-trained machine learning model on the first output, thereby yielding a second output (e.g., 808); computing, by the device (e.g., via 602), an error between the second output and the ground-truth annotation; and updating, by the device (e.g., via 602) and via backpropagation driven by the error, the one or more parameters of the pre-processing transformation, without updating any parameters of the pre-trained machine learning model.

Although not explicitly shown in FIG. 21, the one or more parameters of the pre-processing transformation can be iteratively learned on-the-fly, based on the medical image and based on an auxiliary confidence predictor (e.g., 902). In particular, the computer-implemented method 2100 can further comprise: randomly initializing, by the device (e.g., via 602), the one or more parameters of the pre-processing transformation; executing, by the device (e.g., via 602), the pre-processing transformation on the medical image, thereby yielding a first output (e.g., 1002); executing, by the device (e.g., via 602), the pre-trained machine learning model on the first output, thereby yielding a second output (e.g., 1004); computing, by the device (e.g., via 602) and via execution of the auxiliary confidence predictor, a confidence score for the second output; and updating, by the device (e.g., via 602) and via backpropagation driven by the confidence score, the one or more parameters of the pre-processing transformation, without updating any parameters of the pre-trained machine learning model.

Although not explicitly shown in FIG. 21, the pre-processing transformation can be a linear or non-linear function or machine learning model that takes a pixel or voxel intensity value as an argument, and the one or more parameters can comprise coefficients of the linear or non-linear function or machine learning model.

Although not explicitly shown in FIG. 21, the pre-processing transformation can be a color map assignment, and the one or more parameters can comprise an intensity window and a gamma-value of the color map assignment.

Although not explicitly shown in FIG. 21, the diagnostic or prognostic inferencing task can be medical image classification, medical image segmentation, or medical image regression.

Various embodiments described herein can include a computer program product for facilitating learnable visual prompt engineering. In various aspects, the computer program product can comprise a non-transitory computer-readable memory (e.g., 110) having program instructions embodied therewith. In various instances, the program instructions can be executable by a processor (e.g., 108) to cause the processor to: access an image (e.g., 106); generate an adapted version (e.g., 206) of the image via a pixel-to-pixel or voxel-to-voxel pre-processing transformation (e.g., 202) comprising one or more parameters (e.g., 204) that are iteratively learned; and perform a visual inferencing task, by executing a pre-trained machine learning model (e.g., 104) on the adapted version of the image.

In some cases, the one or more parameters of the pixel-to-pixel or voxel-to-voxel pre-processing transformation can be iteratively learned based on an annotated training dataset (e.g., 604). In other cases, the one or more parameters of the pixel-to-pixel or voxel-to-voxel pre-processing transformation can be iteratively learned on-the-fly (e.g., in the absence of annotated training data), based on the image and based on an auxiliary confidence predictor (e.g., 902).

In various aspects, the pixel-to-pixel or voxel-to-voxel pre-processing transformation can be a linear or non-linear function, a color map assignment, or a machine learning model.

In various instances, machine learning algorithms or models can be implemented in any suitable way to facilitate any suitable aspects described herein. To facilitate some of the above-described machine learning aspects of various embodiments, consider the following discussion of artificial intelligence (AI). Various embodiments described herein can employ artificial intelligence to facilitate automating one or more features or functionalities. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system or environment from a set of observations as captured via events or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events or data.

Such determinations can result in the construction of new events or actions from a set of observed events or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes or systems (e.g., support vector machines, neural networks, expert systems, Bayesian belief networks, fuzzy logic, data fusion engines, and so on) in connection with performing automatic or determined action in connection with the claimed subject matter. Thus, classification schemes or systems can be used to automatically learn and perform a number of functions, actions, or determinations.

A classifier can map an input attribute vector, $z=(z_1, z_2, z_3, z_4, z_n)$, to a confidence that the input belongs to a class, as by f (z)=confidence (class). Such classification can employ a probabilistic or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, or probabilistic classification models providing different patterns of independence, any of which can be employed. Classification as used herein also is inclusive of statistical regression that is utilized to develop models of priority.

Figure 22:
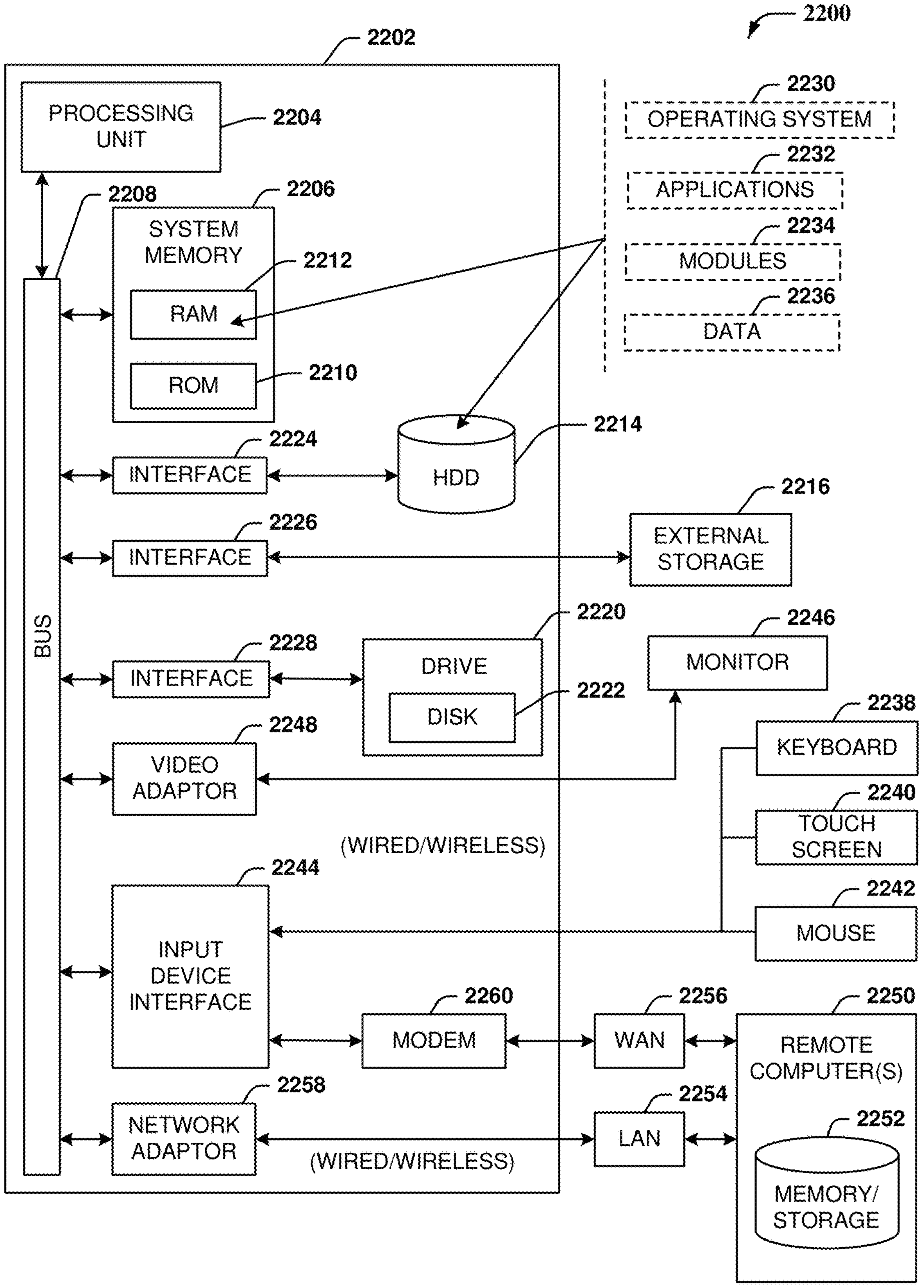
FIG. 22 illustrates a block diagram of an example, non-limiting operating environment in which one or more embodiments described herein can be facilitated.

In order to provide additional context for various embodiments described herein, FIG. 22 and the following discussion are intended to provide a brief, general description of a suitable computing environment 2200 in which the various embodiments of the embodiment described herein can be implemented. While the embodiments have been described above in the general context of computer-executable instructions that can run on one or more computers, those skilled in the art will recognize that the embodiments can be also implemented in combination with other program modules or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multi-processor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network.

In a distributed computing environment, program modules can be located in both local and remote memory storage devices.

Computing devices typically include a variety of media, which can include computer-readable storage media, machine-readable storage media, or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 22, the example environment 2200 for implementing various embodiments of the aspects described herein includes a computer 2202, the computer 2202 including a processing unit 2204, a system memory 2206 and a system bus 2208. The system bus 2208 couples system components including, but not limited to, the system memory 2206 to the processing unit 2204. The processing unit 2204 can be any of various commercially available processors. Dual microprocessors and other multi-processor architectures can also be employed as the processing unit 2204.

The system bus 2208 can be any of several types of bus structure that can further interconnect to a memory bus (with or without a memory controller), a peripheral bus, and a local bus using any of a variety of commercially available bus architectures. The system memory 2206 includes ROM 2210 and RAM 2212. A basic input/output system (BIOS) can be stored in a non-volatile memory such as ROM, erasable programmable read only memory (EPROM), EEPROM, which BIOS contains the basic routines that help to transfer information between elements within the computer 2202, such as during startup. The RAM 2212 can also include a high-speed RAM such as static RAM for caching data.

The computer 2202 further includes an internal hard disk drive (HDD) 2214 (e.g., EIDE, SATA), one or more external storage devices 2216 (e.g., a magnetic floppy disk drive (FDD) 2216, a memory stick or flash drive reader, a memory card reader, etc.) and a drive 2220, e.g., such as a solid state drive, an optical disk drive, which can read or write from a disk 2222, such as a CD-ROM disc, a DVD, a BD, etc. Alternatively, where a solid state drive is involved, disk 2222 would not be included, unless separate. While the internal HDD 2214 is illustrated as located within the computer 2202, the internal HDD 2214 can also be configured for external use in a suitable chassis (not shown). Additionally, while not shown in environment 2200, a solid state drive (SSD) could be used in addition to, or in place of, an HDD 2214. The HDD 2214, external storage device(s) 2216 and drive 2220 can be connected to the system bus 2208 by an HDD interface 2224, an external storage interface 2226 and a drive interface 2228, respectively. The interface 2224 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 2202, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 2212, including an operating system 2230, one or more application programs 2232, other program modules 2234 and program data 2236. All or portions of the operating system, applications, modules, or data can also be cached in the RAM 2212. The systems and methods described herein can be implemented utilizing various commercially available operating systems or combinations of operating systems.

Computer 2202 can optionally comprise emulation technologies. For example, a hypervisor (not shown) or other intermediary can emulate a hardware environment for operating system 2230, and the emulated hardware can optionally be different from the hardware illustrated in FIG. 22. In such an embodiment, operating system 2230 can comprise one virtual machine (VM) of multiple VMs hosted at computer 2202. Furthermore, operating system 2230 can provide runtime environments, such as the Java runtime environment or the .NET framework, for applications 2232. Runtime environments are consistent execution environments that allow applications 2232 to run on any operating system that includes the runtime environment. Similarly, operating system 2230 can support containers, and applications 2232 can be in the form of containers, which are lightweight, standalone, executable packages of software that include, e.g., code, runtime, system tools, system libraries and settings for an application.

Further, computer 2202 can be enable with a security module, such as a trusted processing module (TPM). For instance with a TPM, boot components hash next in time boot components, and wait for a match of results to secured values, before loading a next boot component. This process can take place at any layer in the code execution stack of computer 2202, e.g., applied at the application execution level or at the operating system (OS) kernel level, thereby enabling security at any level of code execution.

A user can enter commands and information into the computer 2202 through one or more wired/wireless input devices, e.g., a keyboard 2238, a touch screen 2240, and a pointing device, such as a mouse 2242. Other input devices (not shown) can include a microphone, an infrared (IR) remote control, a radio frequency (RF) remote control, or other remote control, a joystick, a virtual reality controller or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 2204 through an input device interface 2244 that can be coupled to the system bus 2208, but can be connected by other interfaces, such as a parallel port, an IEEE 1394 serial port, a game port, a USB port, an IR interface, a BLUETOOTH® interface, etc.

A monitor 2246 or other type of display device can be also connected to the system bus 2208 via an interface, such as a video adapter 2248. In addition to the monitor 2246, a computer typically includes other peripheral output devices (not shown), such as speakers, printers, etc.

The computer 2202 can operate in a networked environment using logical connections via wired or wireless communications to one or more remote computers, such as a remote computer(s) 2250. The remote computer(s) 2250 can be a workstation, a server computer, a router, a personal computer, portable computer, microprocessor-based entertainment appliance, a peer device or other common network node, and typically includes many or all of the elements described relative to the computer 2202, although, for purposes of brevity, only a memory/storage device 2252 is illustrated. The logical connections depicted include wired/wireless connectivity to a local area network (LAN) 2254 or larger networks, e.g., a wide area network (WAN) 2256. Such LAN and WAN networking environments are commonplace in offices and companies, and facilitate enterprise-wide computer networks, such as intranets, all of which can connect to a global communications network, e.g., the Internet.

When used in a LAN networking environment, the computer 2202 can be connected to the local network 2254 through a wired or wireless communication network interface or adapter 2258. The adapter 2258 can facilitate wired or wireless communication to the LAN 2254, which can also include a wireless access point (AP) disposed thereon for communicating with the adapter 2258 in a wireless mode.

When used in a WAN networking environment, the computer 2202 can include a modem 2260 or can be connected to a communications server on the WAN 2256 via other means for establishing communications over the WAN 2256, such as by way of the Internet. The modem 2260, which can be internal or external and a wired or wireless device, can be connected to the system bus 2208 via the input device interface 2244. In a networked environment, program modules depicted relative to the computer 2202 or portions thereof, can be stored in the remote memory/storage device 2252. It will be appreciated that the network connections shown are example and other means of establishing a communications link between the computers can be used.

When used in either a LAN or WAN networking environment, the computer 2202 can access cloud storage systems or other network-based storage systems in addition to, or in place of, external storage devices 2216 as described above, such as but not limited to a network virtual machine providing one or more aspects of storage or processing of information. Generally, a connection between the computer 2202 and a cloud storage system can be established over a LAN 2254 or WAN 2256 e.g., by the adapter 2258 or modem 2260, respectively. Upon connecting the computer 2202 to an associated cloud storage system, the external storage interface 2226 can, with the aid of the adapter 2258 or modem 2260, manage storage provided by the cloud storage system as it would other types of external storage. For instance, the external storage interface 2226 can be configured to provide access to cloud storage sources as if those sources were physically connected to the computer 2202.

The computer 2202 can be operable to communicate with any wireless devices or entities operatively disposed in wireless communication, e.g., a printer, scanner, desktop or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Figure 23:
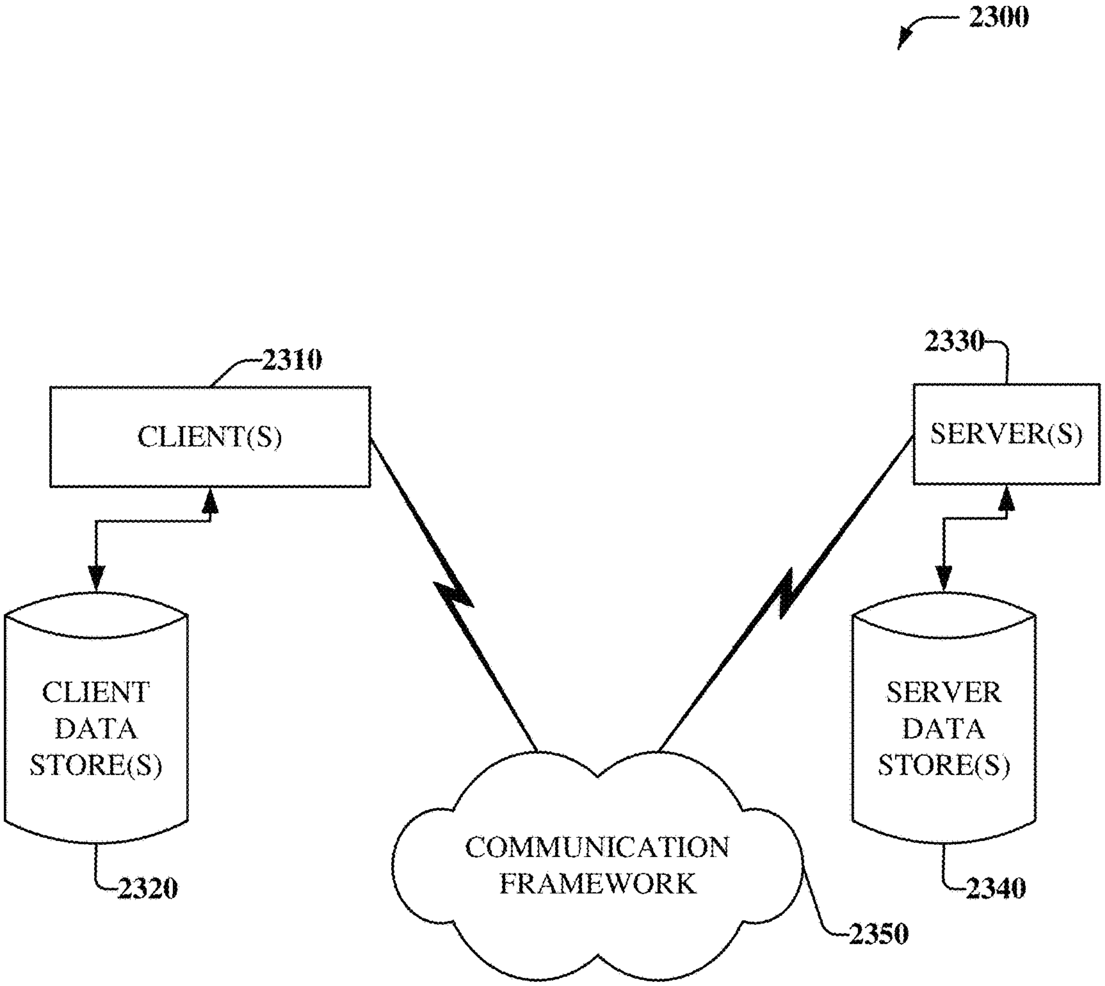
FIG. 23 illustrates an example networking environment operable to execute various implementations described herein.

FIG. 23 is a schematic block diagram of a sample computing environment 2300 with which the disclosed subject matter can interact. The sample computing environment 2300 includes one or more client(s) 2310. The client(s) 2310 can be hardware or software (e.g., threads, processes, computing devices). The sample computing environment 2300 also includes one or more server(s) 2330. The server(s) 2330 can also be hardware or software (e.g., threads, processes, computing devices). The servers 2330 can house threads to perform transformations by employing one or more embodiments as described herein, for example. One possible communication between a client 2310 and a server 2330 can be in the form of a data packet adapted to be transmitted between two or more computer processes. The sample computing environment 2300 includes a communication framework 2350 that can be employed to facilitate communications between the client(s) 2310 and the server(s) 2330. The client(s) 2310 are operably connected to one or more client data store(s) 2320 that can be employed to store information local to the client(s) 2310. Similarly, the server(s) 2330 are operably connected to one or more server data store(s) 2340 that can be employed to store information local to the servers 2330.

Various embodiments may be a system, a method, an apparatus or a computer program product at any possible technical detail level of integration. The computer program product can include a computer readable storage medium (or media) having computer readable program instructions thereon for causing a processor to carry out aspects of various embodiments. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network or a wireless network. The network can comprise copper transmission cables, optical transmission fibers, wireless transmission, routers, firewalls, switches, gateway computers or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various embodiments can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform various aspects.

Various aspects are described herein with reference to flowchart illustrations or block diagrams of methods, apparatus (systems), and computer program products according to various embodiments. It will be understood that each block of the flowchart illustrations or block diagrams, and combinations of blocks in the flowchart illustrations or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart or block diagram block or blocks. These computer readable program instructions can also be stored in a computer readable storage medium that can direct a computer, a programmable data processing apparatus, or other devices to function in a particular manner, such that the computer readable storage medium having instructions stored therein comprises an article of manufacture including instructions which implement aspects of the function/act specified in the flowchart or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart or block diagram block or blocks.

The flowcharts and block diagrams in the Figures illustrate the architecture, functionality, and operation of possible implementations of systems, methods, and computer program products according to various embodiments. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer or computers, those skilled in the art will recognize that this disclosure also can or can be implemented in combination with other program modules. Generally, program modules include routines, programs, components, data structures, etc. that perform particular tasks or implement particular abstract data types. Moreover, those skilled in the art will appreciate that various aspects can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, or a computer. By way of illustration, both an application running on a server and the server can be a component. One or more components can reside within a process or thread of execution and a component can be localized on one computer or distributed between two or more computers. In another example, respective components can execute from various computer readable media having various data structures stored thereon. The components can communicate via local or remote processes such as in accordance with a signal having one or more data packets (e.g., data from one component interacting with another component in a local system, distributed system, or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. As used herein, the term "and/or" is intended to have the same meaning as "or." Moreover, articles "a" and "an" as used in the subject specification and annexed drawings should generally be construed to mean "one or more" unless specified otherwise or clear from context to be directed to a singular form. As used herein, the terms "example" or "exemplary" are utilized to mean serving as an example, instance, or illustration. For the avoidance of doubt, the subject matter disclosed herein is not limited by such examples. In addition, any aspect or design described herein as an "example" or "exemplary" is not necessarily to be construed as preferred or advantageous over other aspects or designs, nor is it meant to preclude equivalent exemplary structures and techniques known to those of ordinary skill in the art.

The herein disclosure describes non-limiting examples. For case of description or explanation, various portions of the herein disclosure utilize the term "each," "every," or "all" when discussing various examples. Such usages of the term "each," "every," or "all" are non-limiting. In other words, when the herein disclosure provides a description that is applied to "each," "every," or "all" of some particular object or component, it should be understood that this is a non-limiting example, and it should be further understood that, in various other examples, it can be the case that such description applies to fewer than "each," "every," or "all" of that particular object or component.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:

a processor that executes computer-executable components stored in a non-transitory computer-readable memory, wherein the computer-executable components comprise:

an access component that accesses a medical image and a pre-trained machine learning model that is configured to perform a diagnostic or prognostic inferencing task;

a visual prompt engineering component that applies a pre-processing transformation to one or more pixels or voxels of the medical image, thereby yielding a transformed version of the medical image, wherein the pre-processing transformation converts an input pixel or voxel intensity value to an output pixel or voxel intensity value via one or more parameters that are iteratively learned by optimizing the one or more parameters while maintaining parameters of the pre-trained machine learning model fixed and using a confidence score generated by an auxiliary confidence predictor as an optimization signal; and an execution component that performs the diagnostic or prognostic inferencing task, by executing the pre-trained machine learning model on the transformed version of the medical image.

2. The system of claim 1, wherein the one or more parameters of the pre-processing transformation are iteratively learned based on an annotated training dataset.

3. The system of claim 2, wherein the annotated training dataset comprises a training medical image corresponding to a ground-truth annotation, and wherein the computer-executable components further comprise:

a training component that:

randomly initializes the one or more parameters of the pre-processing transformation;

executes the pre-processing transformation on the training medical image, thereby yielding a first output;

executes the pre-trained machine learning model on the first output, thereby yielding a second output;

computes an error between the second output and the ground-truth annotation; and updates, via backpropagation driven by the error, the one or more parameters of the pre-processing transformation, without updating any parameters of the pre-trained machine learning model.

4. The system of claim 1, wherein the one or more parameters of the pre-processing transformation are iteratively learned in the absence of annotated training data, based on the medical image and based on the auxiliary confidence predictor.

5. The system of claim 4, wherein the computer-executable components further comprise:

a training component that:

randomly initializes the one or more parameters of the pre-processing transformation;

executes the pre-processing transformation on the medical image, thereby yielding a first output;

executes the pre-trained machine learning model on the first output, thereby yielding a second output;

computes, via execution of the auxiliary confidence predictor, a confidence score for the second output; and updates, via backpropagation driven by the confidence score, the one or more parameters of the pre-processing transformation, without updating any parameters of the pre-trained machine learning model.

6. The system of claim 1, wherein the pre-processing transformation is a linear or non-linear function or machine learning model that takes a pixel or voxel intensity value as an argument, and wherein the one or more parameters comprise coefficients of the linear or non-linear function or machine learning model.

7. The system of claim 1, wherein the pre-processing transformation is a color map assignment, and wherein the one or more parameters comprise an intensity window and a gamma-value of the color map assignment.

8. The system of claim 1, wherein the diagnostic or prognostic inferencing task is medical image classification, medical image segmentation, or medical image regression.

9. A computer-implemented method, comprising:

accessing, by a device operatively coupled to a processor, a medical image and a pre-trained machine learning model that is configured to perform a diagnostic or prognostic inferencing task;

applying, by the device, a pre-processing transformation to one or more pixels or voxels of the medical image, thereby yielding a transformed version of the medical image, wherein the pre-processing transformation converts an input pixel or voxel intensity value to an output pixel or voxel intensity value via one or more parameters that are iteratively learned while parameters of the pre-trained machine learning model remain unchanged and based on a confidence score generated by an auxiliary confidence predictor; and performing, by the device, the diagnostic or prognostic inferencing task, by executing the pre-trained machine learning model on the transformed version of the medical image.

10. The computer-implemented method of claim 9, wherein the one or more parameters of the pre-processing transformation are iteratively learned based on an annotated training dataset.

11. The computer-implemented method of claim 10, wherein the annotated training dataset comprises a training medical image corresponding to a ground-truth annotation, and further comprising:

randomly initializing, by the device, the one or more parameters of the pre-processing transformation;

executing, by the device, the pre-processing transformation on the training medical image, thereby yielding a first output;

executing, by the device, the pre-trained machine learning model on the first output, thereby yielding a second output;

computing, by the device, an error between the second output and the ground-truth annotation; and updating, by the device and via backpropagation driven by the error, the one or more parameters of the pre-processing transformation, without updating any parameters of the pre-trained machine learning model.

12. The computer-implemented method of claim 9, wherein the one or more parameters of the pre-processing transformation are iteratively learned in the absence of annotated training data, based on the medical image and based on the auxiliary confidence predictor.

13. The computer-implemented method of claim 12, further comprising:

randomly initializing, by the device, the one or more parameters of the pre-processing transformation;

executing, by the device, the pre-processing transformation on the medical image, thereby yielding a first output;

executing, by the device, the pre-trained machine learning model on the first output, thereby yielding a second output;

computing, by the device and via execution of the auxiliary confidence predictor, a confidence score for the second output; and updating, by the device and via backpropagation driven by the confidence score, the one or more parameters of the pre-processing transformation, without updating any parameters of the pre-trained machine learning model.

14. The computer-implemented method of claim 9, wherein the pre-processing transformation is a linear or non-linear function or machine learning model that takes a pixel or voxel intensity value as an argument, and wherein the one or more parameters comprise coefficients of the linear or non-linear function or machine learning model.

15. The computer-implemented method of claim 9, wherein the pre-processing transformation is a color map assignment, and wherein the one or more parameters comprise an intensity window and a gamma-value of the color map assignment.

16. The computer-implemented method of claim 9, wherein the diagnostic or prognostic inferencing task is medical image classification, medical image segmentation, or medical image regression.

17. A computer program product for facilitating learnable visual prompt engineering, the computer program product comprising a non-transitory computer-readable memory having program instructions embodied therewith, the program instructions executable by a processor to cause the processor to:

access an image;

generate an adapted version of the image via a pixel-to-pixel or voxel-to-voxel pre-processing transformation comprising one or more parameters that are iteratively learned while parameters of a pre-trained machine learning model remain unchanged and based on a confidence score generated by an auxiliary confidence predictor; and perform a visual inferencing task, by executing the pre-trained machine learning model on the adapted version of the image.

18. The computer program product of claim 17, wherein the one or more parameters of the pixel-to-pixel or voxel-to-voxel pre-processing transformation are iteratively learned based on an annotated training dataset.

19. The computer program product of claim 17, wherein the one or more parameters of the pixel-to-pixel or voxel-to-voxel pre-processing transformation are iteratively learned in the absence of annotated training data, based on the image and based on the auxiliary confidence predictor.

20. The computer program product of claim 17, wherein the pixel-to-pixel or voxel-to-voxel pre-processing transformation is a linear or non-linear function, a color map assignment, or a machine learning or deep learning model.

* * * * *